(12) United States Patent
Yassinzadeh

(10) Patent No.: US 9,427,221 B2
(45) Date of Patent: Aug. 30, 2016

(54) HEMOSTASIS-ENHANCING DEVICE AND METHOD FOR ITS USE

(71) Applicant: Cardiva Medical, Inc., Sunnyvale, CA (US)

(72) Inventor: Zia Yassinzadeh, San Jose, CA (US)

(73) Assignee: Cardiva Medical, Inc., Santa Clara, CA (US)

( * ) Notice: Subject to any disclaimer, the term of this patent is extended or adjusted under 35 U.S.C. 154(b) by 0 days.

(21) Appl. No.: 13/868,775

(22) Filed: Apr. 23, 2013

(65) Prior Publication Data

US 2014/0142547 A1    May 22, 2014

Related U.S. Application Data

(60) Continuation of application No. 12/895,205, filed on Sep. 30, 2010, now Pat. No. 8,444,671, which is a division of application No. 11/614,276, filed on Dec. 21, 2006, now abandoned.

(51) Int. Cl.
*A61B 17/08* (2006.01)
*A61B 17/00* (2006.01)
*A61M 5/168* (2006.01)

(52) U.S. Cl.
CPC ........ *A61B 17/0057* (2013.01); *A61M 5/16881* (2013.01); *A61B 2017/00557* (2013.01); *A61B 2017/00637* (2013.01)

(58) Field of Classification Search
CPC ................. A61B 17/0057; A61B 2017/00637; A61B 2017/00557; A61M 5/16881
See application file for complete search history.

(56) References Cited

U.S. PATENT DOCUMENTS

| 4,744,364 A | 5/1988 | Kensey |
| 4,852,568 A | 8/1989 | Kensey |

(Continued)

FOREIGN PATENT DOCUMENTS

| WO | WO 92/22252 A1 | 12/1992 |
| WO | WO 95/05121 A1 | 2/1995 |

(Continued)

OTHER PUBLICATIONS

International search report and written opinion dated Jun. 13, 2008 for PCT/US2007/087885.

(Continued)

*Primary Examiner* — Gregory Anderson
*Assistant Examiner* — Son Dang
(74) *Attorney, Agent, or Firm* — Wilson, Sonsini, Goodrich & Rosati

(57) ABSTRACT

The present invention advantageously provides devices, systems, and methods for percutaneous access and closure of vascular puncture sites. In an embodiment, the device for enhancing the hemostasis of a puncture site in a body lumen or tract comprises a catheter having one tubular member having a proximal end and a distal end with one inner lumen extending between at least a longitudinal portion of the catheter tubular member. The one tubular member includes external and internal tubular bodies each having proximal and distal ends. At least one of the external and the internal tubular bodies is longitudinally movable with respect to the other. An expansible member with proximal and distal ends is disposed on the distal end of the one tubular member. The distal end of the expansible member is connected to the distal end of internal tubular body and with its proximal end connected to the distal end of external tubular body.

12 Claims, 29 Drawing Sheets

(56) References Cited

U.S. PATENT DOCUMENTS

| | | | |
|---|---|---|---|
| 4,890,612 A | 1/1990 | Kensey |
| 5,061,274 A | 10/1991 | Kensey |
| 5,108,420 A | 4/1992 | Marks |
| 5,108,421 A | 4/1992 | Fowler |
| 5,171,259 A | 12/1992 | Inoue |
| 5,197,971 A | 3/1993 | Bonutti |
| 5,258,000 A | 11/1993 | Gianturco |
| 5,290,552 A | 3/1994 | Sierra et al. |
| 5,292,332 A | 3/1994 | Lee |
| 5,342,393 A | 8/1994 | Stack |
| 5,383,896 A | 1/1995 | Gershony et al. |
| 5,411,520 A | 5/1995 | Nash et al. |
| 5,413,571 A | 5/1995 | Katsaros et al. |
| 5,419,765 A | 5/1995 | Weldon et al. |
| 5,437,631 A * | 8/1995 | Janzen ............ 604/506 |
| 5,454,833 A | 10/1995 | Boussignac et al. |
| 5,456,667 A | 10/1995 | Ham et al. |
| 5,486,195 A | 1/1996 | Myers et al. |
| 5,507,744 A | 4/1996 | Tay et al. |
| 5,626,601 A | 5/1997 | Gershony et al. |
| 5,630,833 A | 5/1997 | Katsaros et al. |
| 5,634,936 A | 6/1997 | Linden et al. |
| 5,728,134 A | 3/1998 | Barak |
| 5,782,860 A | 7/1998 | Epstein et al. |
| 5,810,810 A | 9/1998 | Tay et al. |
| 5,836,913 A | 11/1998 | Orth et al. |
| 5,851,210 A | 12/1998 | Torossian |
| 5,861,003 A | 1/1999 | Latson et al. |
| 5,868,778 A | 2/1999 | Gershony et al. |
| 5,895,398 A | 4/1999 | Wensel et al. |
| 5,906,631 A | 5/1999 | Imran |
| 5,922,009 A | 7/1999 | Epstein et al. |
| 5,951,583 A | 9/1999 | Jensen et al. |
| 5,957,952 A | 9/1999 | Gershony et al. |
| 6,012,457 A | 1/2000 | Lesh |
| 6,017,359 A | 1/2000 | Gershony et al. |
| 6,048,358 A | 4/2000 | Barak |
| 6,056,769 A | 5/2000 | Epstein et al. |
| 6,056,770 A | 5/2000 | Epstein et al. |
| 6,071,300 A | 6/2000 | Brenneman et al. |
| 6,080,182 A | 6/2000 | Shaw et al. |
| 6,146,396 A | 11/2000 | Konya et al. |
| 6,248,124 B1 | 6/2001 | Pedros et al. |
| 6,287,323 B1 | 9/2001 | Hammerslag |
| 6,296,657 B1 | 10/2001 | Brucker |
| 6,315,787 B1 | 11/2001 | Tsugita et al. |
| 6,371,974 B1 | 4/2002 | Brenneman et al. |
| 6,371,975 B2 | 4/2002 | Cruise et al. |
| 6,409,739 B1 | 6/2002 | Nobles et al. |
| 6,464,712 B1 | 10/2002 | Epstein et al. |
| 6,589,269 B2 | 7/2003 | Zhu et al. |
| 6,656,207 B2 | 12/2003 | Epstein et al. |
| 6,913,614 B2 | 7/2005 | Marino et al. |
| 6,949,114 B2 * | 9/2005 | Milo et al. ............ 606/213 |
| 6,994,689 B1 | 2/2006 | Zadno-Azizi et al. |
| 7,025,776 B1 | 4/2006 | Houser et al. |
| 7,044,134 B2 | 5/2006 | Khairkhahan et al. |
| 7,115,127 B2 | 10/2006 | Lindenbaum et al. |
| 7,175,646 B2 | 2/2007 | Brenneman et al. |
| 7,220,246 B2 | 5/2007 | Raulerson et al. |
| 7,223,266 B2 | 5/2007 | Lindenbaum et al. |
| 7,331,976 B2 | 2/2008 | McGuckin, Jr. et al. |
| 7,572,274 B2 | 8/2009 | Yassinzadeh |
| 7,691,127 B2 * | 4/2010 | Yassinzadeh ............ 606/213 |
| 8,444,671 B2 | 5/2013 | Yassinzadeh |
| 2001/0047187 A1 | 11/2001 | Milo et al. |
| 2002/0072767 A1 | 6/2002 | Zhu |
| 2002/0133123 A1 | 9/2002 | Zucker |
| 2003/0055454 A1 | 3/2003 | Zucker |
| 2003/0120291 A1 | 6/2003 | Chin et al. |
| 2003/0187474 A1 | 10/2003 | Keegan et al. |
| 2003/0191493 A1 | 10/2003 | Epstein et al. |
| 2004/0176798 A1 | 9/2004 | Epstein et al. |
| 2005/0228443 A1 | 10/2005 | Yassinzadeh |
| 2005/0267522 A1 | 12/2005 | Yassinzadeh et al. |
| 2005/0277980 A1 | 12/2005 | Yassinzadeh |
| 2006/0195069 A1 | 8/2006 | Opie et al. |
| 2008/0154303 A1 | 6/2008 | Yassinzadeh |

FOREIGN PATENT DOCUMENTS

| | | |
|---|---|---|
| WO | WO 96/24290 A1 | 8/1996 |
| WO | WO 98/34546 A1 | 8/1998 |
| WO | WO 98/40017 A2 | 9/1998 |
| WO | WO 00/06029 A1 | 2/2000 |
| WO | WO 00/06031 A1 | 2/2000 |

OTHER PUBLICATIONS

Office action dated Jun. 24, 2010 for U.S. Appl. No. 11/614,276.
Office action dated Aug. 22, 2012 for U.S. Appl. No. 12/895,205.
Office action dated Oct. 1, 2009 for U.S. Appl. No. 11/614,276.
Notice of allowance dated Feb. 7, 2013 for U.S. Appl. No. 12/895,205.

* cited by examiner

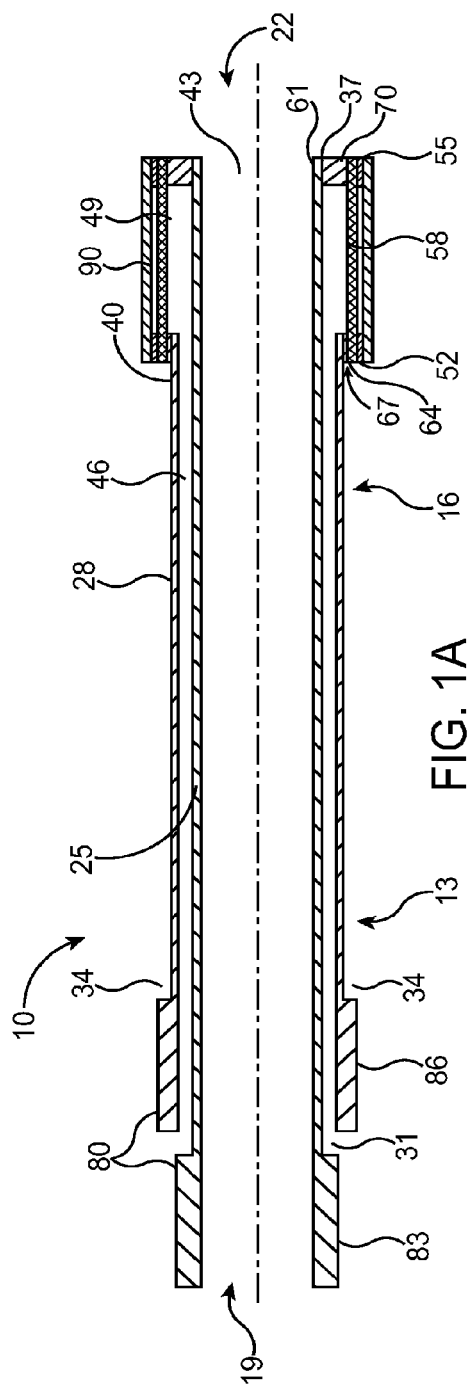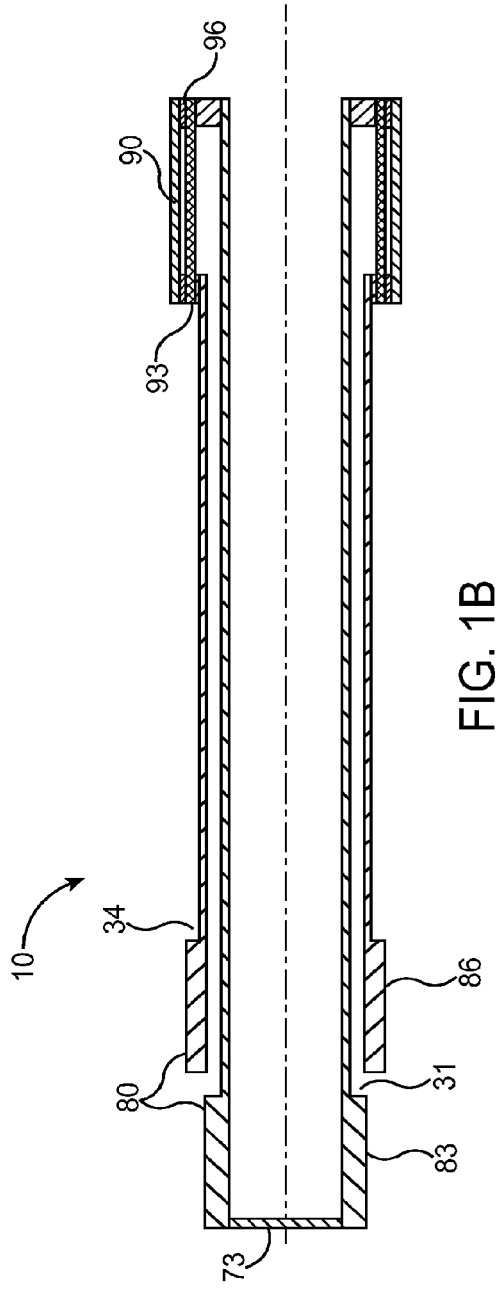

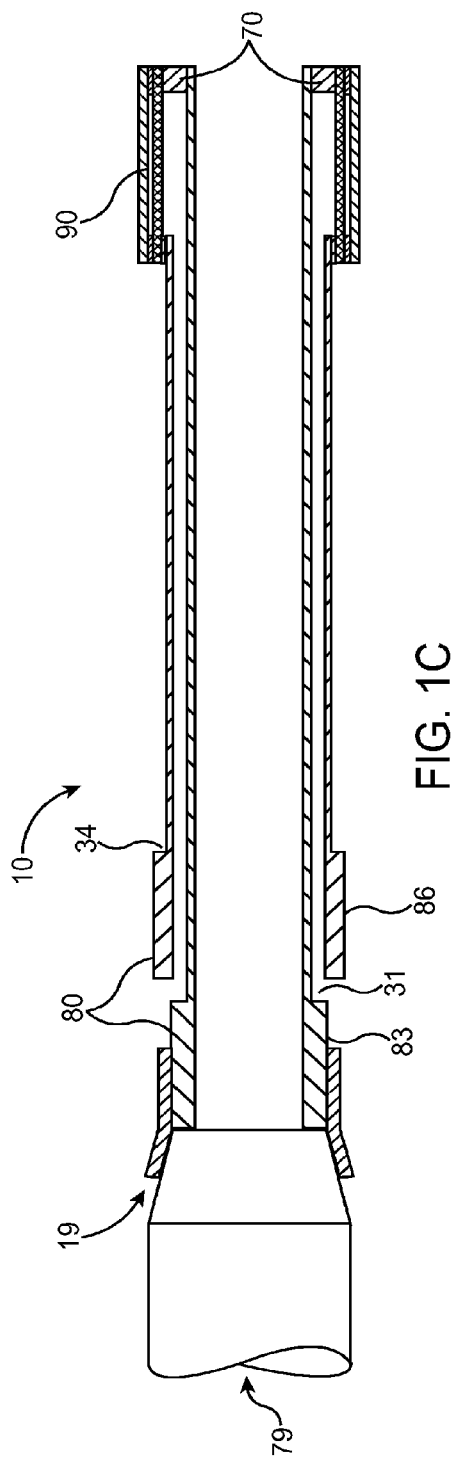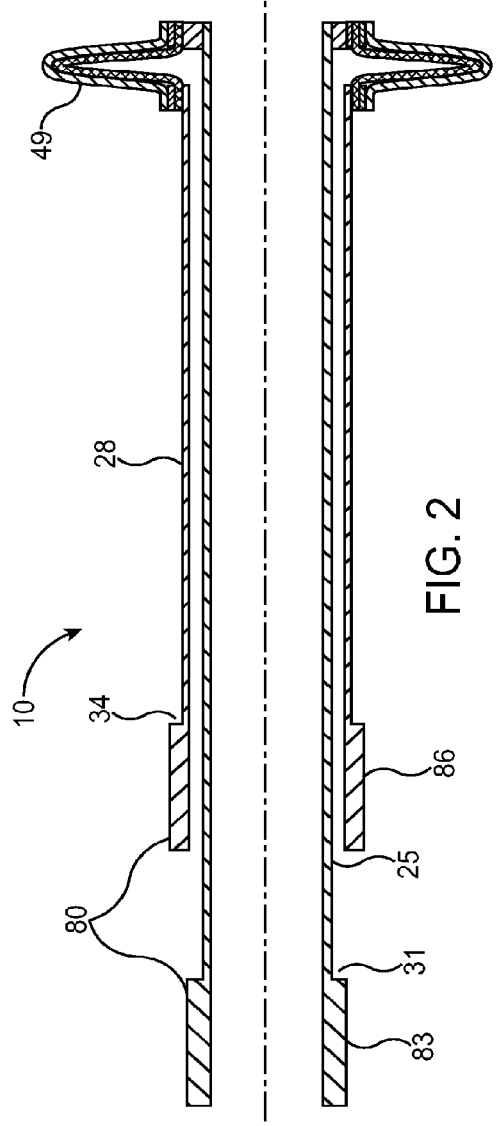

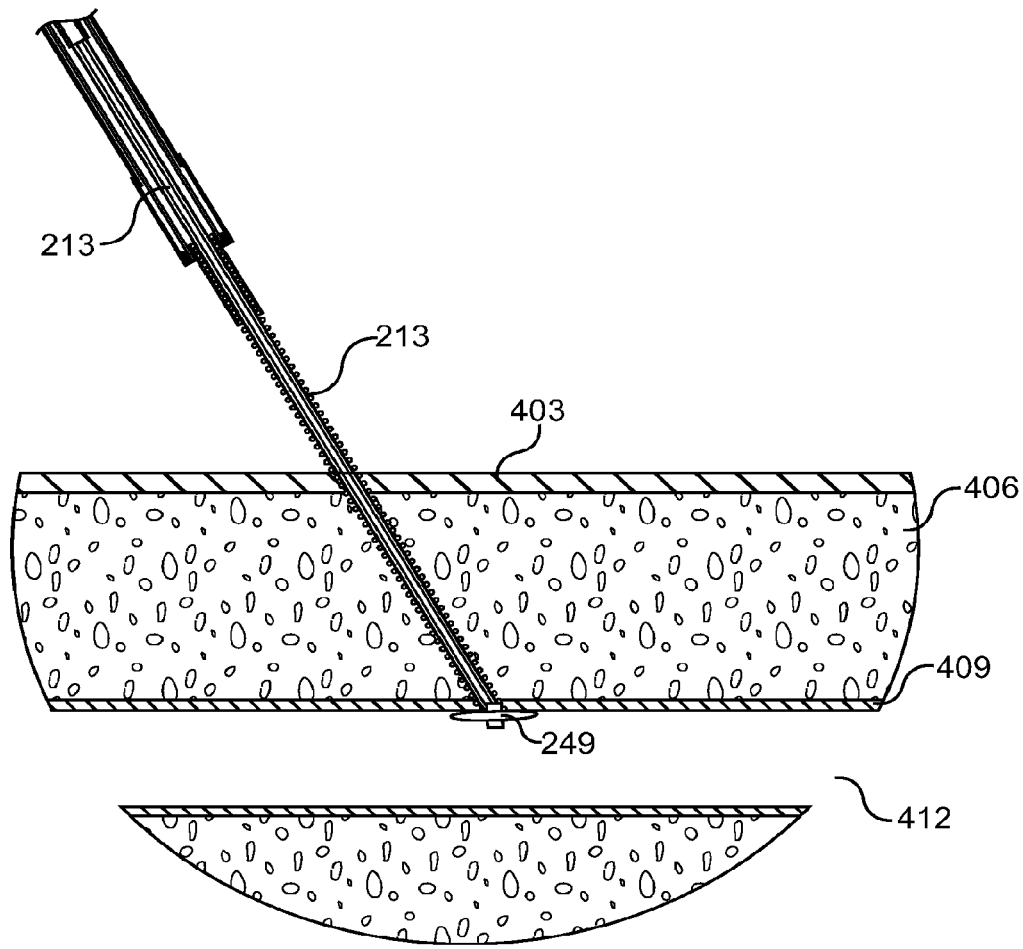
FIG. 13E1

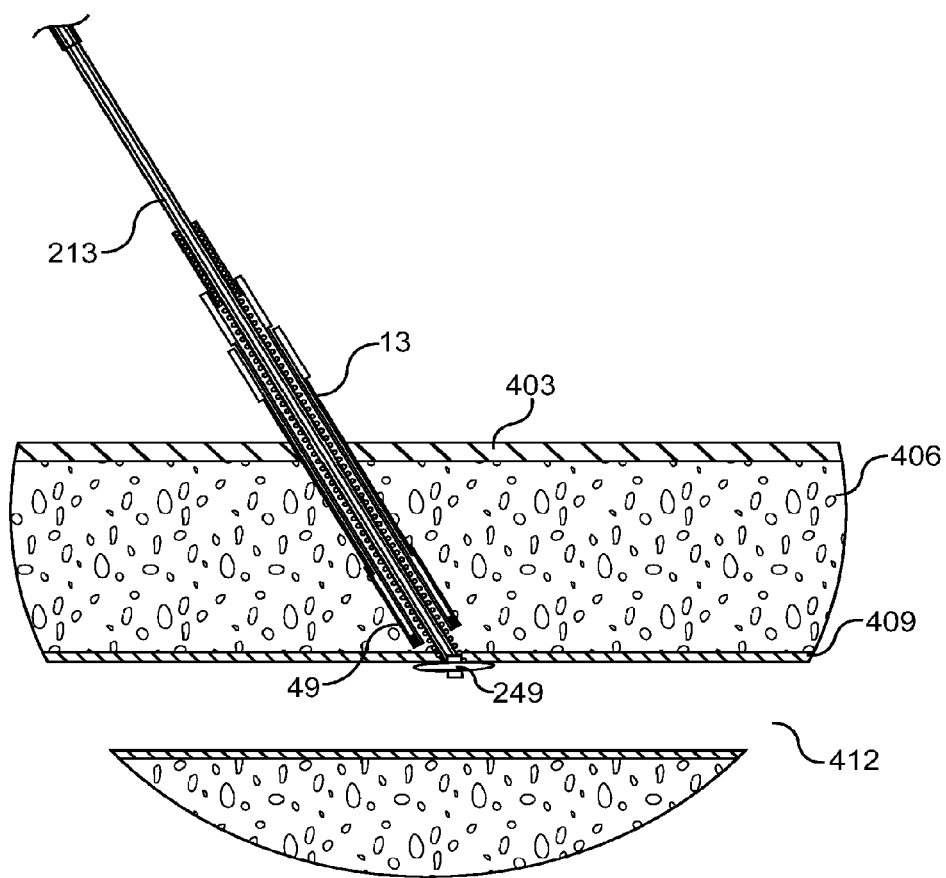
FIG. 13E2

HEMOSTASIS-ENHANCING DEVICE AND METHOD FOR ITS USE

CROSS-REFERENCES TO RELATED APPLICATIONS

The present application is a continuation of U.S. patent application Ser. No. 12/895,205, filed Sep. 30, 2010, which is a divisional of U.S. patent application Ser. No. 11/614,276, filed Dec. 21, 2006, which is related to U.S. patent application Ser. No. 10/974,008, filed on Oct. 25, 2004 (now U.S. Pat. No. 7,993,366); Ser. No. 10/857,177, filed May 27, 2004 (now U.S. Pat. No. 7,572,274); and Ser. No. 10/821,633, filed on Apr. 9, 2004; the full disclosures of which are incorporated herein by reference in their entirety.

BACKGROUND OF THE INVENTION

1. Field of the Invention

The present invention relates generally to devices, systems, and methods for percutaneous sealing of puncture sites in body lumens or tissue tracts. More specifically, the present invention relates to devices, systems, and methods for use in hemostasis of vascular puncture sites.

Percutaneous access of blood vessels in the human body is routinely performed for diagnostics or interventional procedures such as coronary and peripheral angiography, angioplasty, atherectomies, placement of vascular stents, coronary retroperfusion and retroinfusion, cerebral angiograms, treatment of strokes, cerebral aneurysms, and the like. Patients undergoing these procedures are often treated with anti-coagulants such as heparin, thrombolytics, and the like, which make the closure and hemostasis process of the puncture site in the vessel wall at the completion of such catheterization procedures more difficult to achieve.

Various devices have been introduced to provide hemostasis, however none have been entirely successful. Some devices utilize collagen or other biological plugs to seal the puncture site. Alternatively, sutures and/or staples have also been applied to close the puncture site. External foreign objects such as plugs, sutures, or staples however may cause tissue reaction, inflammation, and/or infection as they all "leave something behind" to achieve hemostasis.

There is also another class of devices that use the body's own natural mechanism to achieve hemostasis wherein no foreign objects are left behind. Such devices typically provide hemostasis by sealing the puncture site from the inside of the vessel wall wherein the device is left in place in the vessel lumen until hemostasis is reached and thereafter removed. Although such devices have achieved relative levels of success, removal of the device at times may disrupt the coagulant that is formed at the puncture site. This in turn may cause residual bleeding which requires the device user to apply a few minutes of external manual pressure at the puncture site after the removal of the device to achieve complete hemostasis.

It would be desirable to provide alternative devices, systems, and methods to enhance the hemostasis of a puncture site in a body lumen, particularly blood vessels of the human body. At least some of the these needs are met by the devices, systems, and methods of the present invention described hereinafter.

2. Related Applications

Hemostasis devices for use in blood vessels and tracts in the body are described in co-pending U.S. patent application Ser. Nos. 10/974,008; 10/857,177; 10/821,633; and 10/718,504; and U.S. Pat. Nos. 6,656,207; 6,464,712; 6,056,770; 6,056,769; 5,922,009; and 5,782,860, assigned to the assignee of the present application. The following U.S. patents and Publications may be relevant to the present invention: U.S. Pat. Nos. 4,744,364; 4,852,568; 4,890,612; 5,108,421; 5,171,259; 5,258,000; 5,383,896; 5,419,765; 5,454,833; 5,626,601; 5,630,833; 5,634,936; 5,728,134; 5,836,913; 5,861,003; 5,868,778; 5,951,583; 5,957,952; 6,017,359; 6,048,358; 6,296,657; U.S. Publication Nos. 2002/0133123; 2003/0055454; and 2003/0120291.

The full disclosure of each of the above mentioned references is incorporated herein by reference in its entirety.

BRIEF SUMMARY OF THE INVENTION

The present invention advantageously provides devices, assemblies, and methods for percutaneous access and closure of puncture sites in a body lumen, particularly blood vessels of the human body. It will be appreciated however that application of the present invention is not limited to the blood vasculature, and as such may be applied to any of the vessels, even severely tortuous vessels, ducts, and cavities found in the body as well as tissue tracts. Such closure devices, systems, and methods utilize the body's own natural healing mechanism to achieve complete hemostasis without leaving any foreign objects behind.

In an embodiment, the device for enhancing the hemostasis of a puncture site in a body lumen or tract comprises a catheter having one tubular member having a proximal end and a distal end with one inner lumen extending along at least a longitudinal portion of the catheter tubular member. The one tubular member includes external and internal tubular bodies each having proximal and distal ends. At least one of the external and the internal tubular bodies is longitudinally movable with respect to the other. An expansible member with proximal and distal ends is disposed on the distal end of the one tubular member. The distal end of the expansible member is attached to the distal end of internal tubular body, while the proximal end of the expansible member is attached to the distal end of external tubular body.

In an embodiment, the expansible member is expanded by the longitudinal movement of the internal and external tubular bodies with respect to one another. In an embodiment, the expansion is achieved by maintaining the internal tubular body in position while moving the external tubular body distally with respect to the internal tubular body. The degree of expansion of the expansible member in an embodiment is based on the longitudinal displacement between the external and the internal tubular bodies.

In an embodiment, the expansible member comprises a mesh layer, spring, coil, slotted tube, coiled string, or braided filament such as one with small pores.

In an embodiment, distal and proximal spacers are disposed at the distal ends of the external and internal tubular bodies, connecting the external and the internal tubular bodies with the proximal and the distal ends of the expansible members; respectively. The outer diameter of the expansible member at the distal and proximal ends may be similar or different (e.g., greater or smaller). In an embodiment, the difference between the outer diameter of the expansible member at its proximal and distal ends affects the direction of the movement of the expansible member upon its expansion. In an embodiment, when the outer diameter at the distal end is less than that at the proximal end, it enables the expansible member to fold forward (in the distal direction) upon expansion. The change in the outer diameter at the distal end of the expansible member may be achieved by providing a distal spacer having a smaller thickness than the proximal spacer, or removing the distal spacer in total.

In an embodiment, the internal tubular body of the one catheter is configured for fluid communication; at its distal end with the body lumen; and at its proximal end with a mechanism for removal of bodily fluids, such as blood, from the body. The fluid body removal mechanism, may be a syringe or syringe/hemostatic valve mechanism as commonly available.

In an embodiment, the one catheter is advanced to the body through a puncture site at the skin, tissue/fascia, and then the body lumen. The one expansible member is thereafter expanded intraluminally and seated against a vessel wall. In an embodiment the expansible member is expanded by the internal tubular body moving the external tubular body distally relative to the internal tubular body and subsequently placed against the vessel site at the puncture site. The expansible member may be allowed to remain in the body lumen until the puncture site has healed, after which the expansible member is collapsed and removed slowly from the human body. During the operation, the optional syringe may be used to withdraw bodily fluids using the lumen of the internal tubular body of the one catheter.

In an embodiment, the one expansible member of the one catheter is advanced to the tissue/fascia, and expanded extraluminally within the fascia along a tissue tract of the puncture site. In an embodiment, the expansible member is expanded by maintaining the internal tubular body stationary while moving the external tubular body distally and thereafter removed upon achieving the desired effect.

In an embodiment, another catheter having another tubular member with proximal and distal ends and another expansible member with proximal and distal ends disposed on the distal end of the another tubular member is provided. The inner diameter of the internal tubular body of the one catheter and the outer diameter of the tubular member of the another catheter are configured such that the another catheter is disposable within the lumen of the internal tubular body of the one catheter.

The one and the another catheters may be advanced simultaneously or separately within the body. The expansible members may be, independently, disposed within the body lumen and the tissue/fascia. The expansible members may be expanded simultaneously or sequentially in any order as appropriate. Similarly, the expansible members may be unexpanded and retracted from the body lumen and/or the tissue/fascia as necessary.

In an embodiment, the one and the another catheters are pre-loaded into one another (e.g., the one catheter is disposed over the another catheter) forming a catheter assembly. As described above, the one and the another catheter may be advanced simultaneously or separately to within the body. The expansible members may be, independently, disposed within the body lumen and the tissue/fascia. The expansible members may be expanded simultaneously or sequentially in any order as appropriate. Similarly, the expansible members may be unexpanded and retracted from the body lumen and/or the tissue/fascia as necessary.

In an embodiment, either or both of the expansible members may be at least partially covered with a flexible membrane.

In the operation, in most embodiments, at the completion of a procedure, such as a catheterization procedure, an introducer sheath is disposed through an opening in a skin surface, tissue tract in fascia, and a vessel wall, and is seated in a vessel lumen.

The one and the another catheter may be introduced alone without the use of the other, or they may be used in conjunction with one another. When used in conjunction with one another, each of the catheters may be introduced together with the other, separately, sequentially, or as an integrated system to the patient's body. In most embodiment, either or both the one and the another catheter are introduced directly or indirectly through the introducer sheath. Either or both the expansible members, independently, may be expanded intraluminally or extraluminally within the tissue/fascia. In some embodiments, a syringe may be used to draw bodily fluids, such as blood, from the body lumen through the lumen of the internal tubular body.

In an embodiment, the one catheter is introduced through the sheath and the expansible member is advanced into and deployed within the body lumen. The introducer sheath is then slowly withdrawn from the body, leaving the one expansible member in expanded position seating against the vessel wall at the puncture site within the body lumen. The one catheter including the one expansible member is left in the body lumen as long as necessary to allow the body's own natural wound healing mechanism to achieve hemostasis, after which it is removed from the patient's body.

In an embodiment, the one catheter is introduced through the sheath and the expansible member is a advanced into the body lumen. The introducer sheath is then slowly withdrawn from the body, leaving the one catheter and the one expansible member in place. The another catheter is then inserted through the proximal end of the one catheter. The another expansible member is advanced within the body lumen to a position distal of the one expansible member. The expansible members are deployed, simultaneously, or separately (in any order desired). The another expansible member is then contracted and the another catheter is pulled proximally and removed from the body through the lumen of the one catheter, leaving the one catheter and the expansible member seating against the vessel wall at the puncture site within the body lumen as long as necessary to allow the body's own natural wound healing mechanism to achieve hemostasis, after which it is removed from the patient's body. Alternatively, the one expansible member may be contracted and removed from the body lumen first, leaving the another expansible member in place as long as necessary before withdrawing it from the patient's body.

In another embodiment, the another catheter of an assembly comprising both the one and the another catheters, is preloaded within the lumen of the internal tubular body of the one catheter. The distal end of the assembly is then inserted through the sheath and the assembly (including both the one and another catheters) is advanced through an opening in skin, and through tissue tract. The another catheter is advanced until the another expansible member is disposed within the body lumen while the one catheter's expansible member is placed at a predetermined distance from the vessel wall within the tissue/fascia. The introducer sheath is then slowly pulled proximally and retracted from the body lumen, with the one and another expansible members located in the tissue/fascia and the body lumen, respectively. The one and the another expansible members are then expanded in their respective locations, with the one expansible member in the tissue/fascia and the another expansible member seating against the vessel wall at the puncture site within the body lumen. The another expansible member is then contracted and the another catheter is then pulled proximally and removed from the body through the lumen of the one catheter, leaving the one catheter and the one expansible member in the tissue fascia as long as necessary to allow the body's own natural wound healing mechanism to achieve hemostasis, after which it is removed from the patient's body. Alternatively, the one expansible member may be contracted and removed from the body lumen first, leaving the another expansible member in place as long as necessary before withdrawing it from the patient's body.

In another embodiment, the another catheter is preloaded within the lumen of internal tubular body of the one catheter forming the assembly of the two catheters. The distal end of the assembly is then inserted through a hub of the sheath, thereby advancing the assembly through an opening in skin, and through the tissue tract, and within the body lumen. With the one and the another expansible members positioned within the body lumen and expanded, the one expansible member rests against the vessel wall at the puncture site, while the another expansible member is placed against the distal end of the one expansible member. The introducer sheath is then slowly pulled proximally and retracted from the body lumen, leaving the first and second catheters in place within the body lumen. The one expansible member is then contracted and the one catheter is then pulled proximally and removed from the body over the another catheter, leaving the another catheter and the another expansible member in the body lumen as long as necessary to allow the body's own natural wound healing mechanism to achieve hemostasis, after which it is removed from the patient's body. Alternatively, the another expansible member may be contracted and removed from the body lumen first, leaving the one expansible member in place as long as necessary before withdrawing it from the patient's body.

In another embodiment, the another catheter of the device is inserted through the existing sheath, advancing the another expansible member within the body lumen. The another expansible member is then expanded by holding the distal handle part of another catheter handle assembly stationary and moving the proximal handle part proximally. The introducer sheath is then slowly pulled proximally and retracted from the body lumen, leaving the another catheter in place with the another expansible member in expanded position seating against the vessel wall at the puncture site within the body lumen. The proximal end of the another catheter is pushed through the distal end of the one catheter and fed through the lumen of its internal tubular body until it exists the proximal end of the one catheter. The one catheter is then guided over the tubular member of the another catheter through an opening in skin, through tissue tract, until its distal end is placed at a predetermined distance from the vessel wall and against subcutaneous tissue. The one expansible member is then expanded over the puncture site of the vessel wall by pulling the handle of the external tubular body proximally while maintaining the internal tubular body of the one catheter substantially stationary. The another expansible member is then contracted and the another catheter is then pulled proximally and removed from the body through the lumen of the one catheter, leaving one catheter and the one expansible member in the tissue fascia as long as necessary to allow the body's own natural wound healing mechanism to achieve hemostasis, after which it is removed from the patient's body.

As can be appreciated, the catheters of assembly may be advanced, expanded, and retracted from the patient's body in any order as may be necessary. Additionally, each of the one expansible member and the another expansible members, when used in combination with one another, may, independently, be expanded within the body lumen or within the tissue/fascia.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIG. 1A illustrates a device for enhancing the hemostasis of a puncture site in a body lumen or tract embodying features of the present invention and having an expandable member at a distal end.

FIG. 1B illustrates an alternative design of the device of FIG. 1 having a seal at a proximal end of the device.

FIG. 1C illustrates an alternative design of the device of FIG. 1 having a detachable syringe at a proximal end of the device for removal of bodily fluids to and from the body lumen.

FIG. 2 illustrates the device of FIG. 1 showing the expandable member in an expanded position.

FIGS. 13A through 13G illustrate the method of FIGS. 12A through H, with the devices shown in longitudinal cross sectional views.

DETAILED DESCRIPTION OF THE INVENTION

Figure 3:
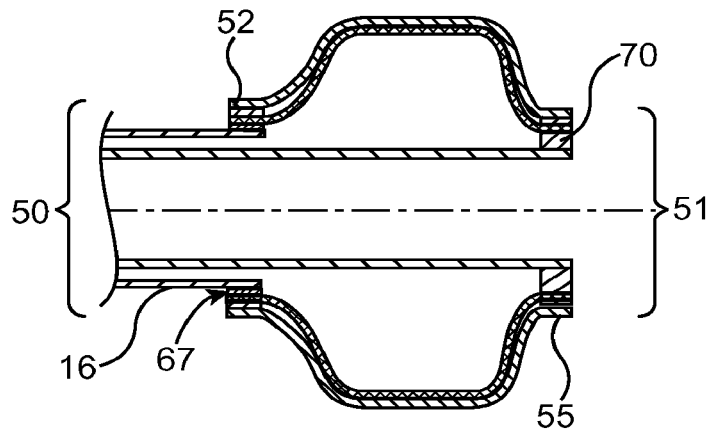
FIGS. 3-5 illustrate exemplary embodiments of the expansible member of the device of FIG. 1, in expanded configuration.

FIGS. 1A through 1C and FIG. 2 (in an expanded configuration), illustrate a hemostasis-enhancing device 10 embodying features of the present invention and generally comprising one catheter 13 having one tubular member 16 with proximal and distal ends 19 and 22, one elongated internal tubular body 25, and one elongate external tubular body 28 slidably disposed over the internal tubular body 25. The inner and external tubular bodies 25 and 28, each respectively has proximal ends 31 and 34, distal ends 37 and 40, and inner lumens 43 and 46 extending between the proximal and distal ends of each body. The distal end 40 of the external tubular body 28 is proximally set apart at a longitudinal distance from the distal end 37 of the internal tubular body. It will be appreciated that the above depictions, as shown, are for illustrative purposes only and do not necessarily reflect the actual shape, size, or dimensions of the device 10. This applies to all depictions hereinafter. In an embodiment, the inner and/or the outer elongate bodies 25 and 28 may be independently chosen to be flexible or rigid.

One expansible member 49 with proximal and distal ends 52 and 55, and an intermediate portion 58 disposed therebetween, is disposed at the distal end of the hemostasis-enhancing device 10. The distal end 55 of the one expansible member 49 is sealingly secured to the distal end 37 of the internal tubular body 25 at a distal connection point 61, and the proximal end 52 of the one expansible member is sealingly secured to the distal end 40 of the external tubular body 28 at a proximal connection point 64; respectively. The proximal and distal ends 52 and 55 of the one expansible member 49 may be separated from the outer and internal tubular bodies 25 and 28, by way of proximal and distal spacers 67 and 70; respectively. The connection of the one expansible member 49 with the inner and external tubular bodies may be made with a crimp process, use of shrink tubing such as polyester tubing, adhesives such as glue, heat staking member into member, or a combination thereof.

Optionally, as shown in FIG. 1B, a seal 73 may be disposed at the proximal end of the internal tubular body 25, or any other suitable position along the length thereof. The seal, by way of example, may be made of any self-sealing material and may include a cross-cut to enable the insertion and/or withdrawal of other elongate members from the lumen 43 of the internal tubular body 25. The one catheter at the proximal end 19, as shown in FIG. 1C, may be equipped with a suitable connector 79 for attaching a syringe (not shown) or the like to deliver fluids to or from the body lumen. By way of example, the syringe may be used to withdraw bodily fluids, such as blood, from the body lumen during the procedure.

Now referring to FIG. 2, the one expansible member is shown in expanded configuration with the proximal end 34 of the external tubular body 28 being distally spaced apart from the proximal end 31 of the internal tubular body 25, causing the radial expansion of the one expansible member 49.

Figure 4:
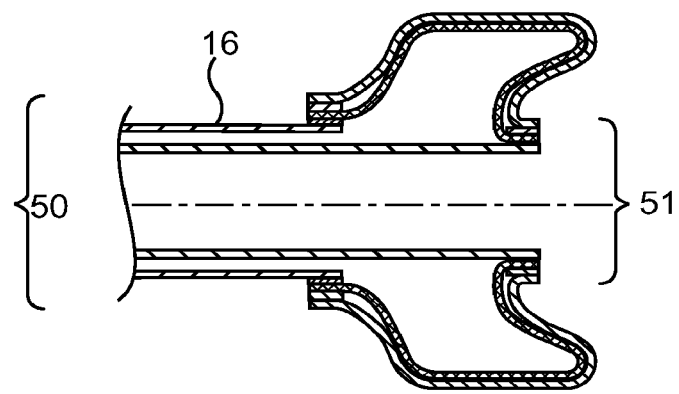
Figure 5:
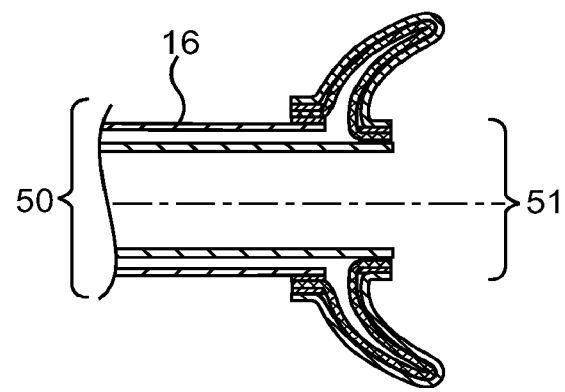

In an embodiment, features of which are shown in FIG. 3, the outer diameters 50 and 51 of the one tubular member 16 at the proximal and distal ends 52 and 55 of the expansible member are substantially similar, with the thickness of the distal spacer 70 being greater than that of the proximal spacer 67. In this configuration, the expansible member, substantially and uniformly expands upon expansion. Alternatively, as shown in FIG. 4, the outer diameter of the one tubular member 16 at the proximal end 52 of the one expansible member 49 is greater than that at the expansible member distal end 55. In another alternate embodiment, as shown in FIG. 5, the outer diameter of the one tubular member 16 at the proximal end of the expansible member 49 is relatively much greater than that at the expansible member distal end 55. As can be noted, the difference in the outer diameter of the one tubular member 16 at the proximal and distal ends of the expansible member affect the shape of the expansible member upon expansion. By way of example, as can be seen in FIG. 5, the smaller outer diameter at the distal end of the expansible member, enables the expansible member to fold in the proximal direction upon expansion. The proximal and distal spacers may be used to provide the desired outer diameter relationship at the proximal and distal ends of the expansible member. In some embodiments, the length of the expansible member may configured to provide the desired shape upon expansion (e.g., disc or cylinder).

As further shown in FIGS. 1A and 1B, a handle assembly 80 may be removably connectable at the proximal end 19 of the one catheter 13. In an embodiment, a proximal part 83 of the handle is connectable to the proximal end 31 of the internal tubular body 25 and a distal part 86 is connectable to the proximal end 34 of the external tubular body 28. Handle parts 83 and 86 provide for an enhanced grip on the device 10, allowing the user to more conveniently move either or both the inner and the external tubular bodies with respect to the other for the purpose of deploying and retracting the expansible member. In an embodiment, the external tubular body is longitudinally movable while the internal tubular body is maintained substantially stationary.

The one catheter 13 and its inner and external tubular bodies may be formed from solid or coiled stainless steel tubing or polymer materials such as nylon, polyurethane, polyimide, PEEK®, PEBAX®, and the like. The catheter may have a length in a range from about 5 centimeters ("cm") to about 50 cm, preferably in the range from about 10 cm to about 40 cm; and a diameter in the range from about 0.5 millimeters ("mm") to about 0.6 mm, preferably in the range from about 1 mm to about 4 mm. The inner diameter of the internal tubular body 25, in an embodiment, is sufficiently large to enable housing of another catheter within, as described further below with respect to FIG. 6.

The maximum outer diameter of the external tubular body of the one catheter, in an embodiment, when the device is used through indwelling sheath is chosen to be less than the inside diameter of an introducer sheath. For example, when a 5 Fr (French) sheath is used, the maximum diameter of the external tubular body of the one catheter would be less than 1.75 mm. The smaller this difference, the greater the interference between the external tubular body of the one catheter and the sheath.

The one expansible member 49 in a retracted or unexpanded state has a diameter of less than about 10 mm, preferably less than about 4 mm, as shown in FIG. 1A. When deployed, the one expansible member 49 in an expanded state has a diameter in a range from about 2 mm to about 25 mm, preferably from about 4 mm to about 15 mm, as shown in FIG. 2 (or the other expanded embodiments shown). The expanded diameter, as referenced, is measured at the largest nominal external diameter, as for example, at the intermediate portion 58. Exemplary expansible member structures are described in detail in U.S. Pat. No. 5,836,913 and co-pending U.S. patent application Ser. No. 10/718,504, both assigned to the assignee of the present application and incorporated herein by reference in their entirety.

The expansible member 49 may comprise a variety of structures including a braided filament, mesh layer, spring, coil, slotted tube, or balloon. Optionally, as shown in FIG. 1A, a deformable membrane 90 may be at least partially disposed over the one expansible member 49. However, in the case where the expansible member comprises a braided mesh, the braid may be sufficiently tight such that without the use of a membrane in a deployed state, it can adequately occlude the puncture site in the vessel. The expansible member may also be coated with a highly hydrophobic coating such as TEFLON® or HYDRO-SIL®. The combination of small pores in the braided mesh and high surface tension of the expansible member achieved by the use of such coatings may provide an adequate barrier to blood flow through the puncture site. The expansible member occludes the vascular surface at the puncture site without substantially disturbing the blood flow to the lower extremities.

The optional membrane 90 may be formed from a variety of medical grade materials, such as thermoplastic elastomers (e.g., CHRONOPRENE® or POLYBLEND®) having durometers in a range from 15 A to about 40 A. Adhesives such as LOCTITE® 4014 may be used to attach the optional membrane to the one catheter tubular body 16 at the proximal and distal connection points, 93 and 96. Alternatively, the membrane may take a form of a sock having its distal end sealed through a heat stake process or the like. In this case, the membrane may not have to be attached distally. The optional membrane preferably has a diameter that is sufficient to cover the expansible member. In some embodiments, the membrane may be designed and attached to facilitate one expansible member expansion as well as to reduce the amount of required elongation and the stretch of the membrane when the expansible member is deployed. This may be achieved by molding the membrane so that its midpoint diameter, where deployed expansible member has its greatest diameter, is larger than its proximal and distal end diameters (e.g., a spherical shape). The membrane may also be formed like a tube with a larger diameter than needed (diameter of retracted expansible member), and then stretched over the expansible member and attached. The stretch should be enough to reduce the diameter of the membrane to that of the expansible member. In such a case, when the one expansible member is deployed, there is less elongation and stress experienced by the membrane. The membrane may additionally form a membrane tip (not shown) at the distal end of the catheter so as to provide a soft and blunt point for percutaneous access. In other embodiments, a flexible tip deflector may be coupleable to the catheter body distal the expansible member so as to prevent any damage to the surrounding vessel wall. The use of the membrane is preferred when the expansible member is used for intraluminal expansion within a target site in the body of the patient.

Figure 6:
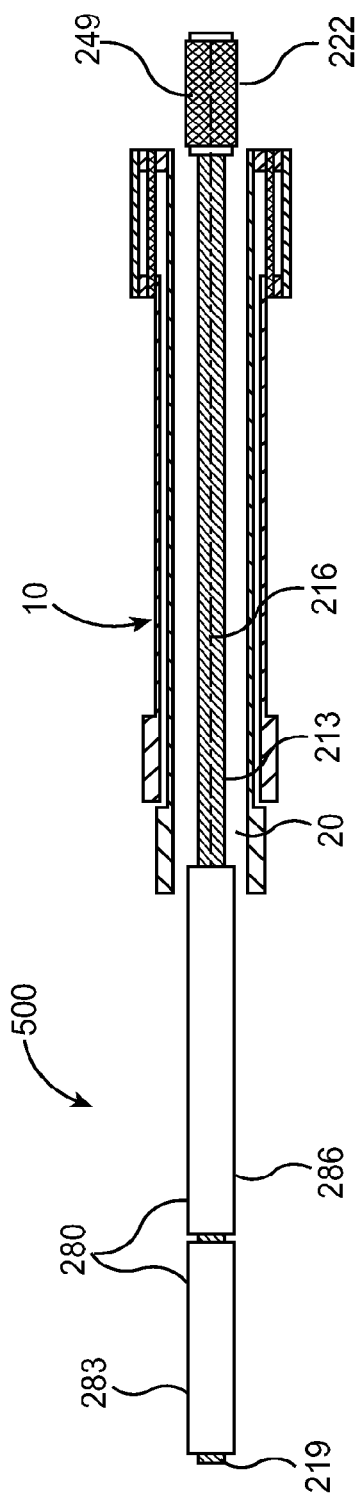
FIG. 6 illustrates an assembly for enhancing the hemostasis of a puncture site in a body lumen or tract embodying features of the present invention and including the device of FIG. 1 and another device disposed within the first device.
Figure 7:
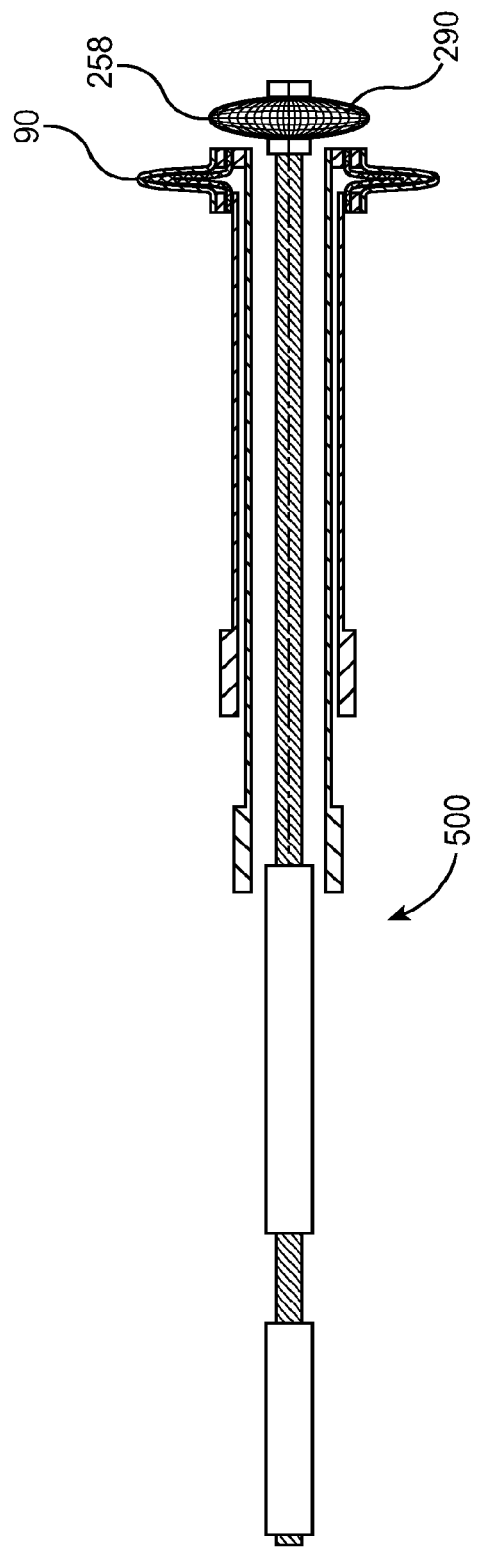
FIG. 7 illustrates the device of FIG. 6 showing the expandable members in an expanded position.

Referring now to FIGS. 6-7, a hemostasis-enhancing assembly 500, wherein like references represent like elements, includes the hemostasis-enhancing device 10, and another device 20 generally comprising another flexible catheter 213 that is slidably disposable within the internal tubular body 25 of the one catheter 13. The another catheter 213 may be removably disposable within the inner lumen of the one catheter or the two catheters may be integrally formed with one another, forming a single catheter assembly 500.

The another flexible catheter 213, as shown, generally includes another elongate tubular member 216 with proximal and a distal ends 219 and 222. The another catheter 213 may be of any suitable construction as for example, detailed in co-pending U.S. patent application Ser. No. 10/974,008, filed on Oct. 25, 2004; Ser. No. 10/857,177, filed May 27, 2004; Ser. No. 10/821,633, filed on Apr. 9, 2004; the full disclosures of which are incorporated herein by reference in their entirety.

The another catheter's elongate tubular member 216 may be formed from coiled stainless steel tubing or polymer materials such as nylon, polyurethane, polyimide, PEEK®, PEBAX®, and the like. The another elongate tubular member 216 may have a length in a range from about 10 cm to about 50 cm, preferably in the range from about 15 cm to about 30 cm and a diameter in the range from about 0.25 mm to about 5 mm, preferably in the range from about 0.5 mm to about 2 mm. Another expansible member 249 is disposed at the distal end 222 of the another elongate member. Exemplary expansible member structures are described in detail in co-pending U.S. patent application Ser. No. 10/974,008 filed on Oct. 25, 2004, assigned to the assignee of the present application and incorporated herein by reference in its entirety.

The another expansible member 249 in a retracted or unexpanded state has an outer diameter of less than about 5 mm, preferably less than about 3 mm, as shown in FIG. 6. When deployed, the another expansible member 249 in an expanded state has an outer diameter in a range from about 2 mm to about 25 mm, preferably from about 3 mm to about 10 mm, as shown in FIG. 7. The expanded diameter, as referenced, is measured at the largest nominal external diameter, as for example, at an intermediate portion 258.

The another expansible member, may similar to the one expansible member, be, at least partially, covered by another optional membrane 290, as described in reference to the one expansible member, and with independently selected features or characteristics as described above.

Another handle assembly 280 may be removably connectable at the proximal end 219 of the another elongate member 216. In an embodiment, handle parts 283 and 286 provide for an enhanced grip on the device 20, allowing the user to more conveniently move the another elongate member 216 in and out of the one catheter 10, as well as deploying and retracting the another expansible member 249. The longitudinal movement of the proximal handle part 283 of the another elongate member 216 will enable the deployment or retraction of the another expansible member 249. The another expansible member 249 may comprise a push or a pull type deployment means as is described in detail in co-pending U.S. patent application Ser. No. 10/821,633, filed on Apr. 9, 2004, assigned to the assignee of the present application and incorporated herein by reference in its entirety. Exemplary expansible member structures are described in detail in co-pending U.S. patent application Ser. No. 10/718,504, filed on Nov. 19, 2003, assigned to the assignee of the present application and incorporated herein by reference in its entirety. Still further embodiments of other expansible braided mesh members are disclosed in U.S. Pat. No. 5,836,913, also incorporated herein by reference in its entirety.

The operation and use of device 10 alone or in combination with device 20, as separate devices, or as assembly 500, are described below. As can be appreciated, many of the details previously described do not necessarily appear in the method figures for purposes of clarity.

Figure 8A:
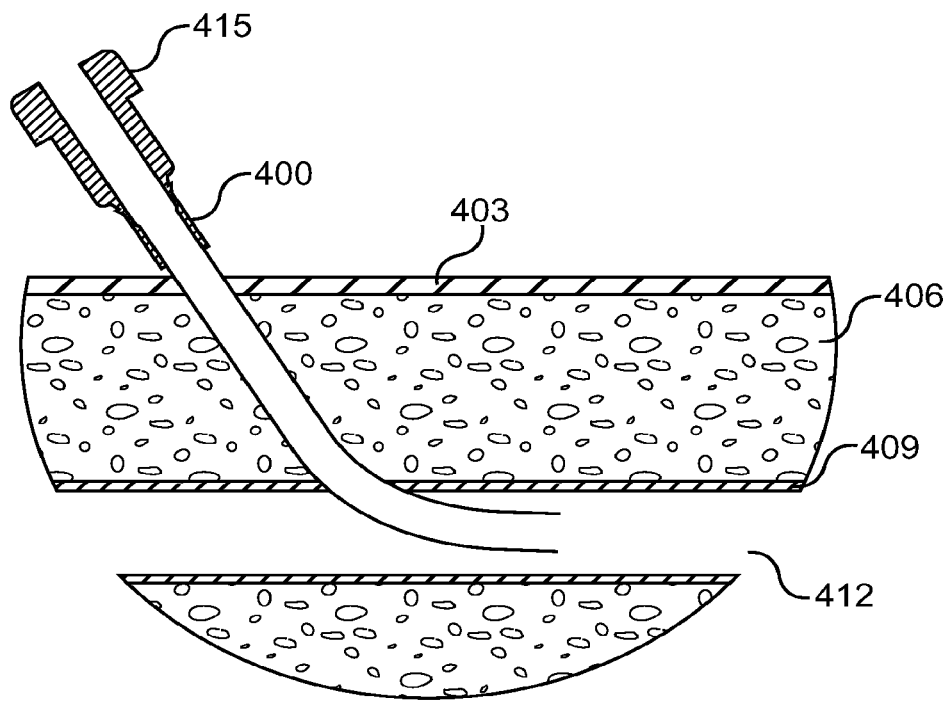
FIGS. 8A though 8E illustrate an exemplary method for hemostasis of a puncture site in a body lumen employing the device of FIG. 1.

Referring to FIGS. 8A through 8E, features of an exemplary method for hemostasis of a puncture site in a body lumen employing the device of FIGS. 1A through 1C are illustrated. FIG. 8A depicts an existing introducer sheath 400 disposed through an opening in a skin surface 403, tissue tract in fascia 406, and vessel wall 409 and seated in a vessel lumen 412, at the completion of a catheterization procedure.

Figure 8B:
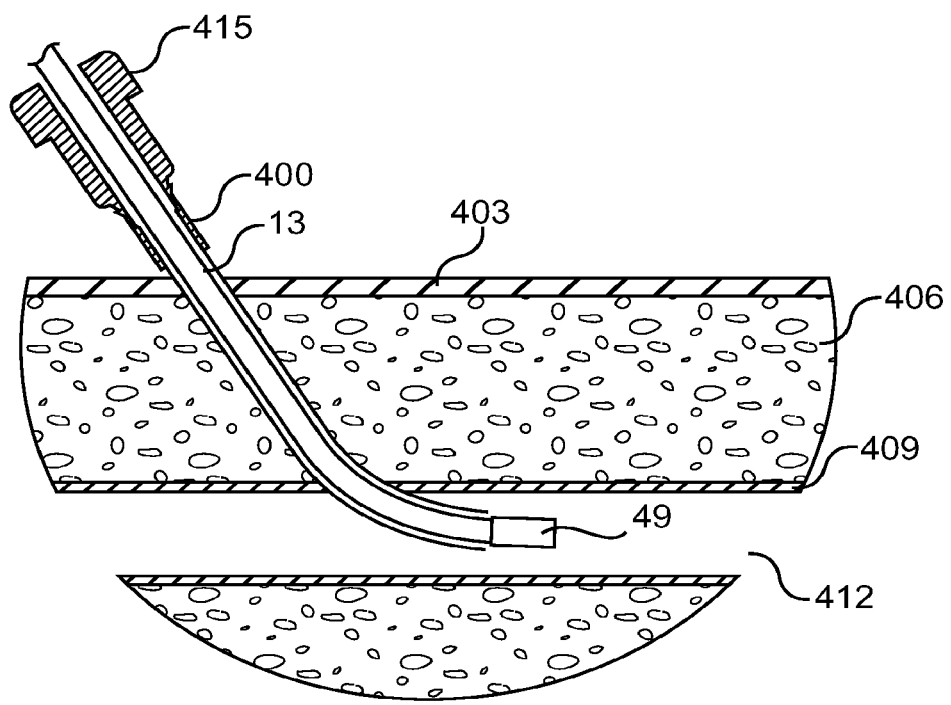
Figure 8C:
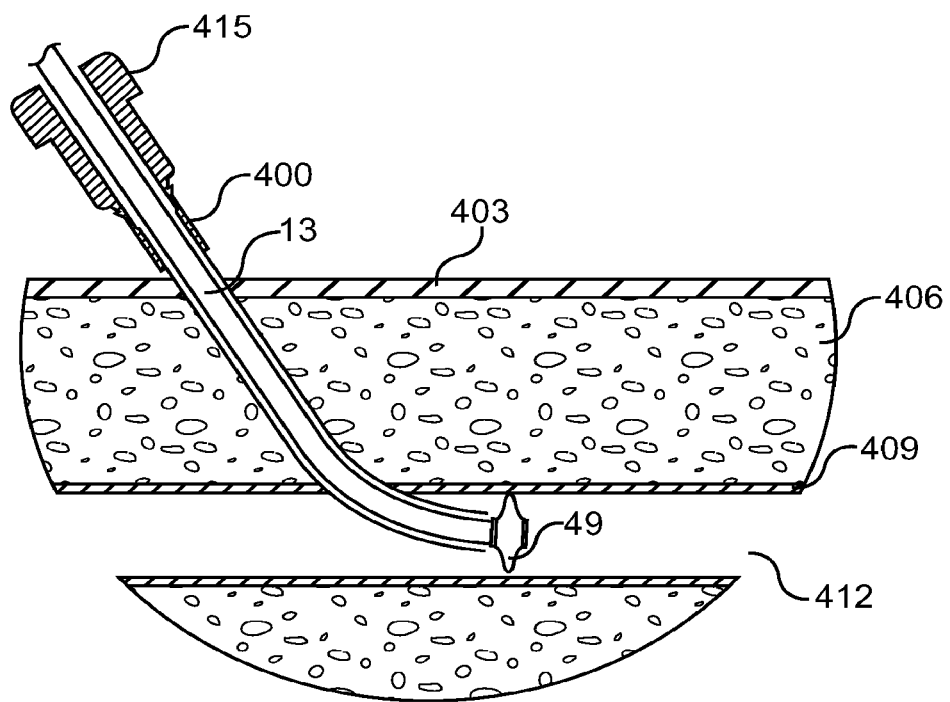
Figure 8D:
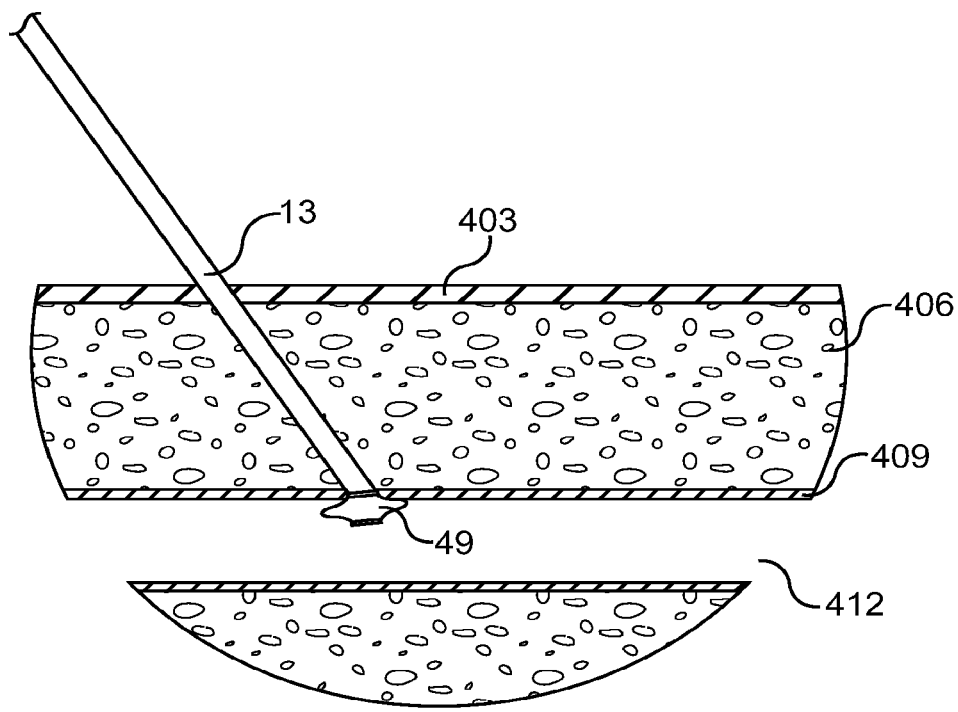
Figure 8E:
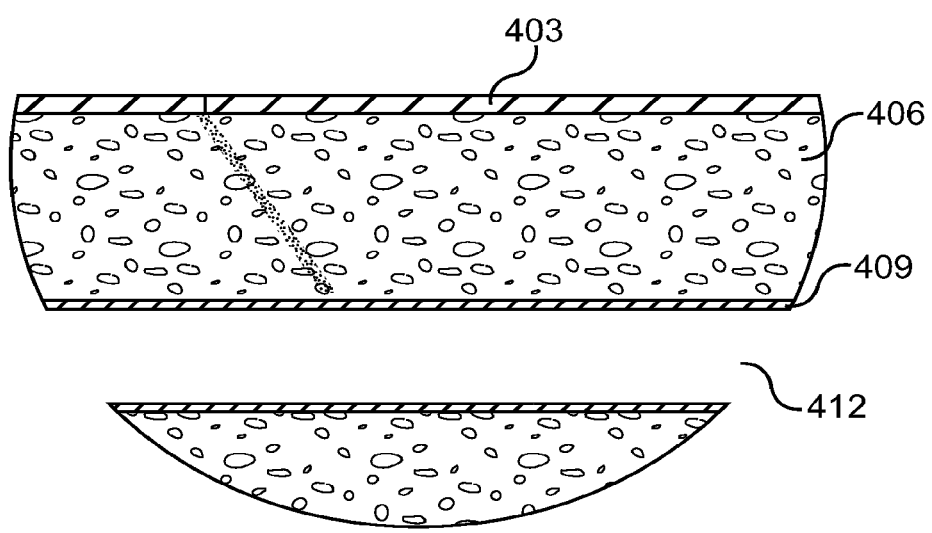

The device 10 (e.g., of FIG. 1A), is then inserted through a hub 415 of the sheath 400 to a marking, such as when the distal end of the distal handle part 86 of the one catheter 10 rests against the hub of the sheath, as shown in FIG. 8B, thereby advancing the one expansible member 49 within the body lumen 412. As shown in FIG. 8C, the one expansible member 49 is then deployed within the body lumen by moving the proximal handle part 83 of the one catheter handle assembly 80 relative to the distal handle part 86, as described relative to FIGS. 1 and 2. The introducer sheath 400 is then slowly pulled proximally and retracted (not shown) from the body lumen, leaving the one catheter in place with the one expansible member in expanded position seating against the vessel wall at the puncture site within the body lumen. The one catheter including the one expansible member 49 is left in body lumen as long as necessary to allow the body's own natural wound healing mechanism to achieve hemostasis (FIG. 8D), after which it is removed from the patient's body (FIG. 8E). During the procedure, the syringe (not shown), may be used to draw bodily fluids, such as blood, from the body lumen through the lumen of the internal tubular body 25.

Figure 9A:
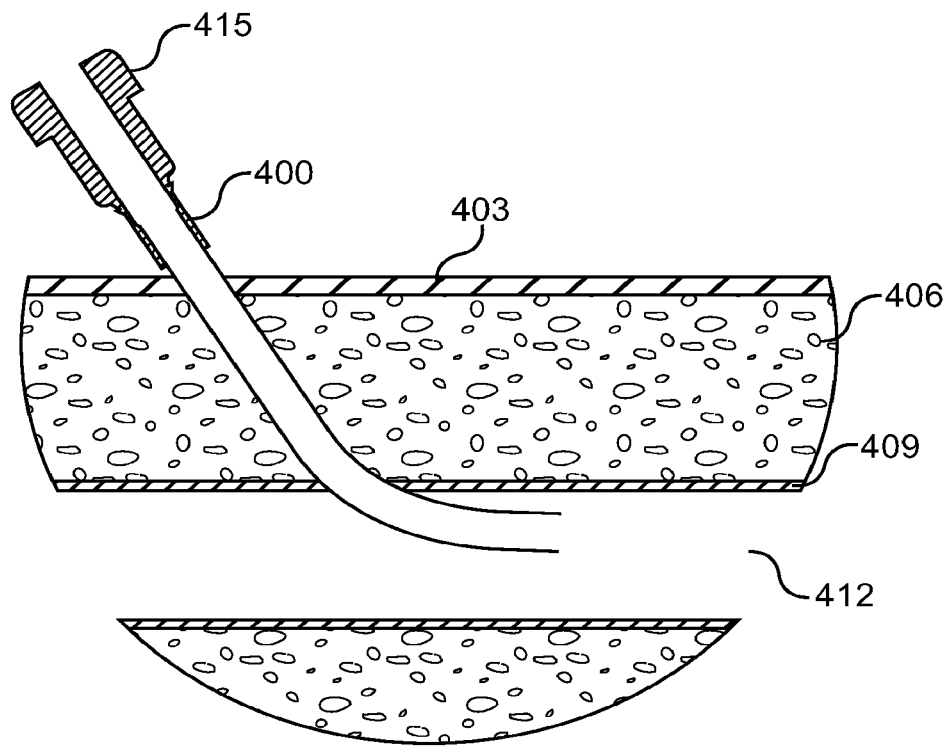
FIGS. 9A though 9G illustrate an exemplary method for hemostasis of a puncture site in a body lumen employing the devices shown in FIG. 6.

Referring now to FIGS. 9A through 9G, features of an exemplary method for hemostasis of a puncture site in a body lumen employing the devices 10 and 20 of FIGS. 6-7 is illustrated. FIG. 9A depicts an existing introducer sheath 400 disposed through an opening in a skin surface 403, tissue tract in fascia 406, and vessel wall 409 and seated in a vessel lumen 412, at the completion of a catheterization procedure.

Figure 9B:
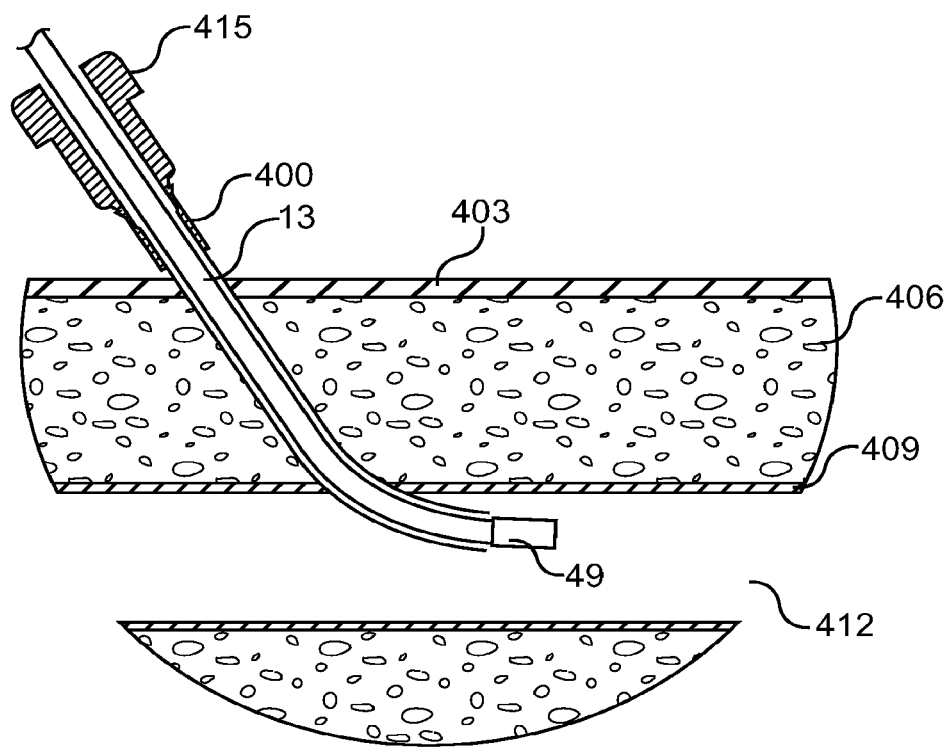
Figure 9C:
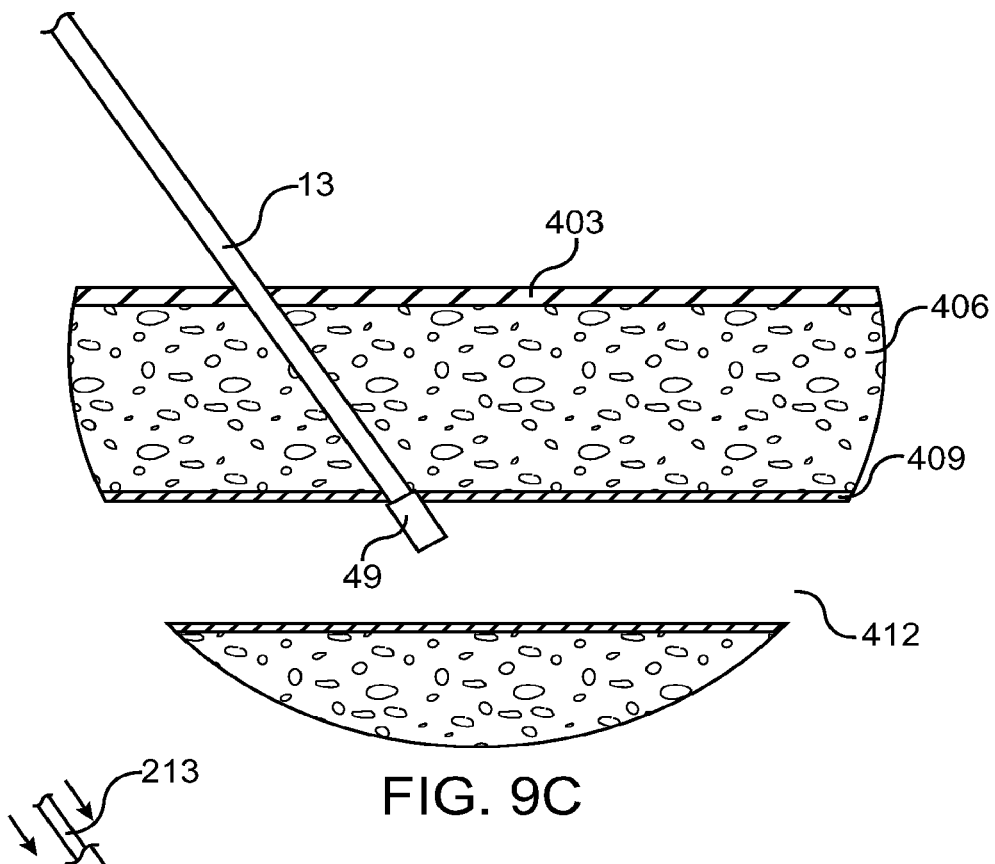

The device 10 (e.g., of FIG. 1A), is then inserted through a hub 415 of the sheath 400 to a marking, such as when the distal end of the distal handle part 86 of the one catheter 10 rests against the hub of the sheath, as shown in FIG. 9B, thereby advancing the one expansible member 49 within the body lumen. The introducer sheath is then slowly pulled proximally and retracted (not shown) from the body lumen, leaving the one catheter in place (FIG. 9C).

Figure 9D:
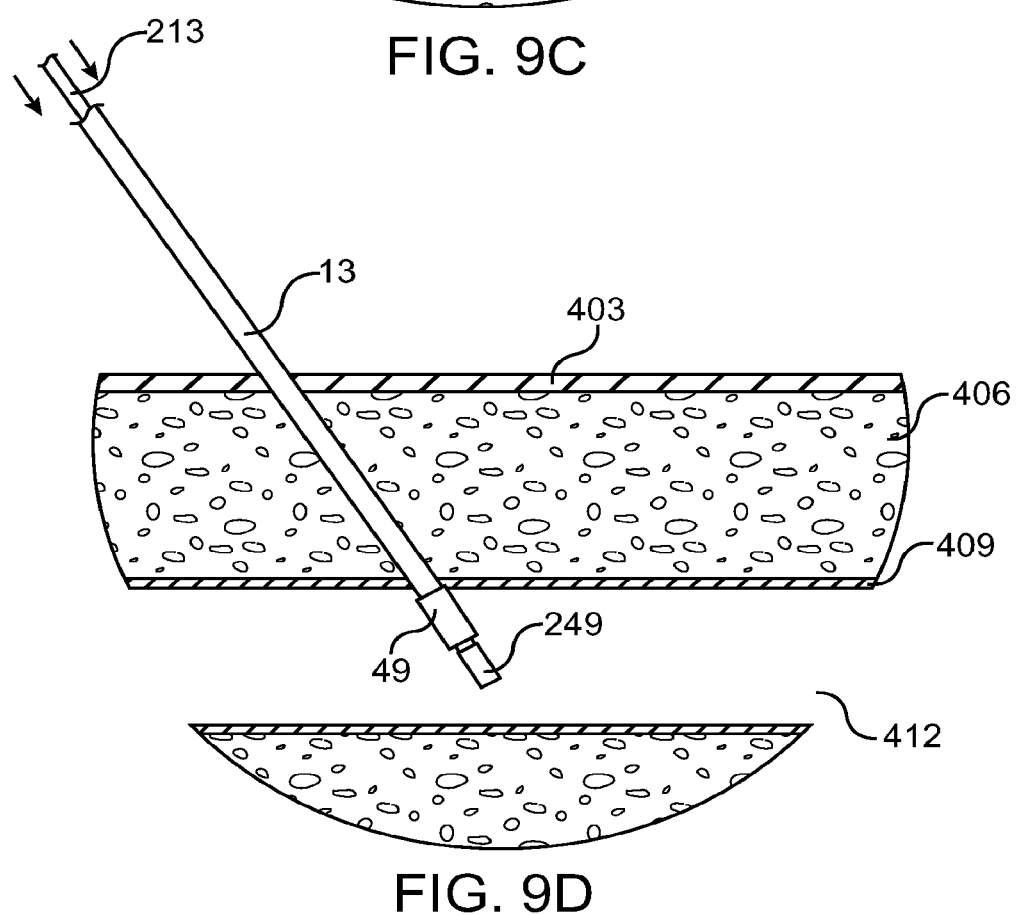
Figure 9E:
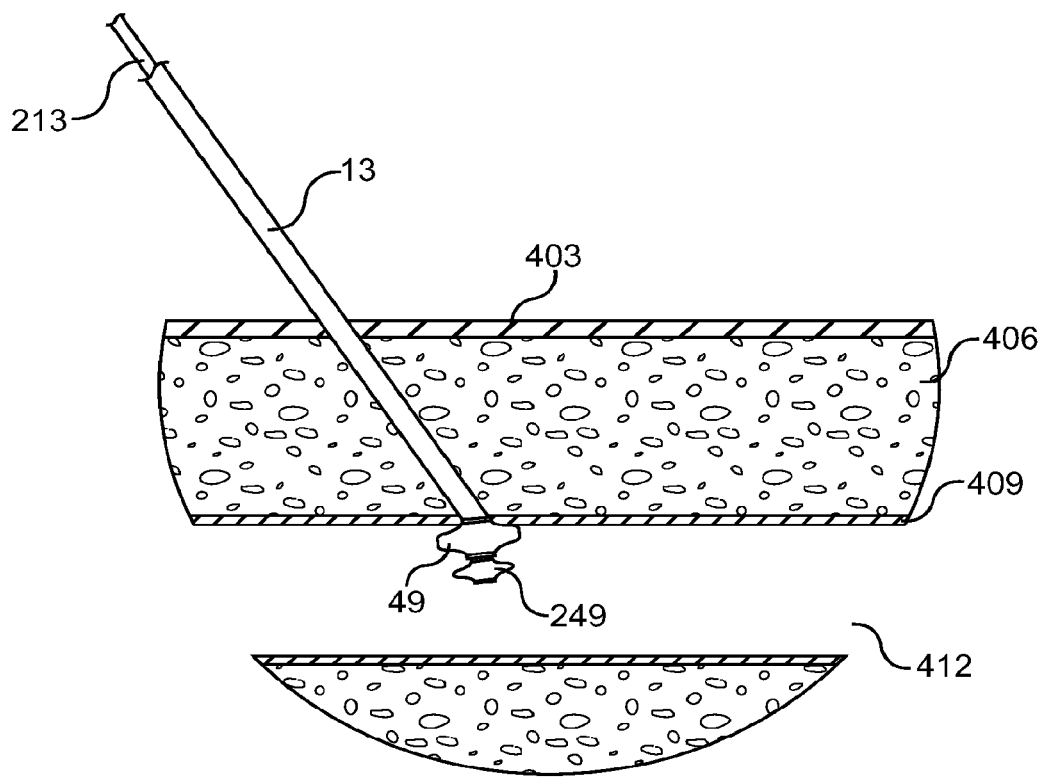
Figure 9F:
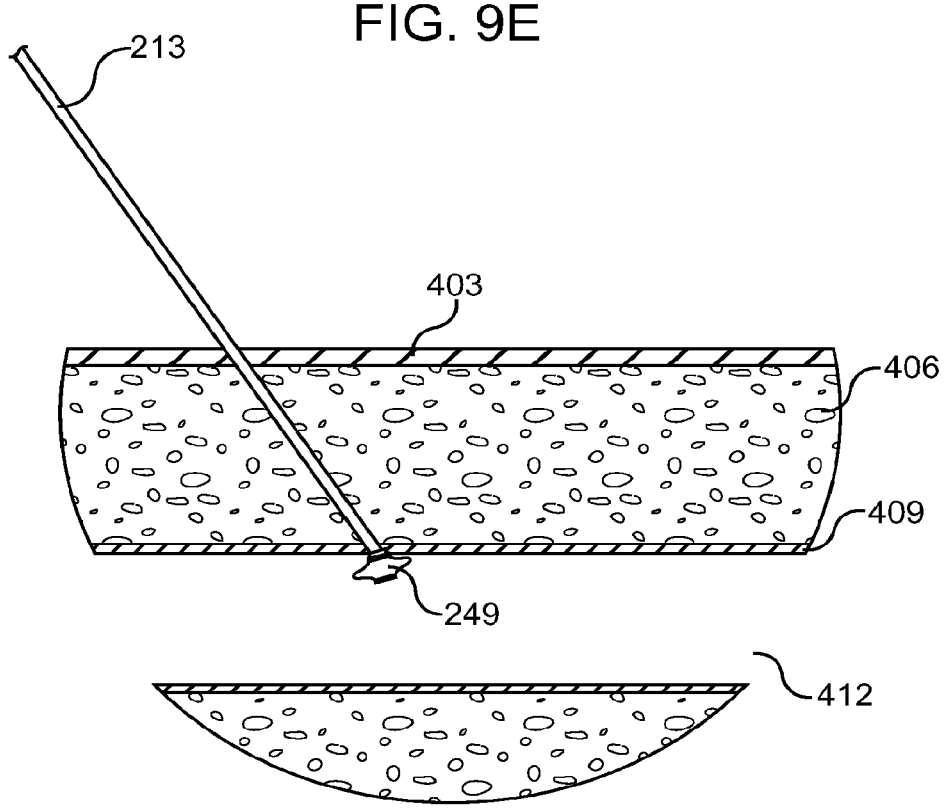

The another catheter 213 of the device 20 is then inserted through the proximal end 19 of the one catheter 13 (e.g., seal 73 of one catheter of FIG. 1B), thereby advancing the another expansible member 249 distal to the one expansible member and within the body lumen (FIG. 9D). As shown in FIG. 9E, the expansible members 49 and 249 are then both deployed, simultaneously or separately (in any order as desired, as for example first expanding the another expansible member followed by expansion of the one expansible member or vice versa). In some embodiments, the one catheter 13 and the another catheter 213 are pulled proximally to place the expansible member 49 against the vessel wall and the another expansible member 249 against the distal opening of the one catheter 13, so that in combination, the two catheters can help achieve sufficient blockage of the puncture site.

Figure 9G:
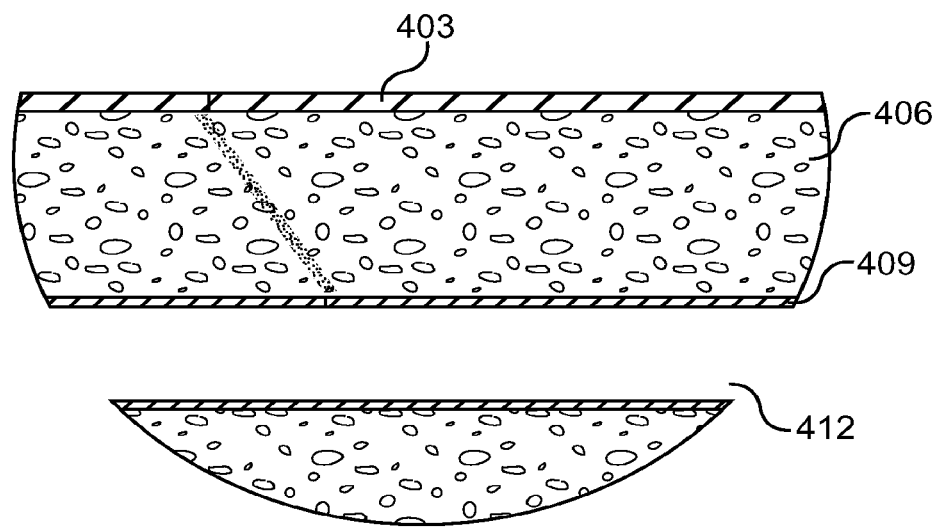

The expansible member 49 is then contracted and catheter 13 is then pulled proximally and removed from the body (not shown) over catheter 213, leaving the catheter 213 and the expansible member 249 seating against the vessel wall at the puncture site within the body lumen (FIG. 9F) as long as necessary to allow the body's own natural wound healing mechanism to achieve hemostasis, after which catheter 213 is removed from the patient's body (FIG. 9G). During the procedure, a syringe (not shown), may be used to draw bodily fluids, such as blood, from the body lumen through the lumen of the internal tubular body 25. Alternatively, the expansible member 249 may be contracted and removed from the body lumen first, leaving the expansible member 49 in place as long as necessary before withdrawing it from the patient's body.

Figure 10A:
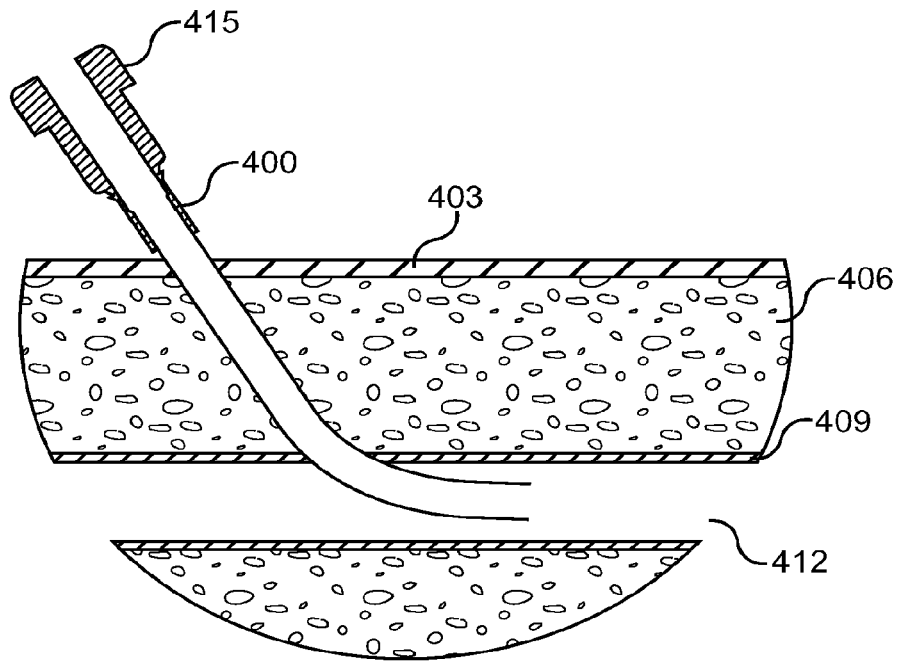
FIGS. 10A though 10F illustrate an exemplary method for hemostasis of a puncture site in a body lumen employing the devices shown in FIG. 6.

Referring to FIGS. 10A through 10F, features of an exemplary method for hemostasis of a puncture site in a body lumen employing the assembly 500 comprising devices 10 and 20 of FIGS. 6-7 is illustrated. FIG. 10A depicts an existing introducer sheath 400 disposed through an opening in a skin surface 403, tissue tract in fascia 406, and vessel wall 409 and seated in a vessel lumen 412, at the completion of a catheterization procedure.

Figure 10B:
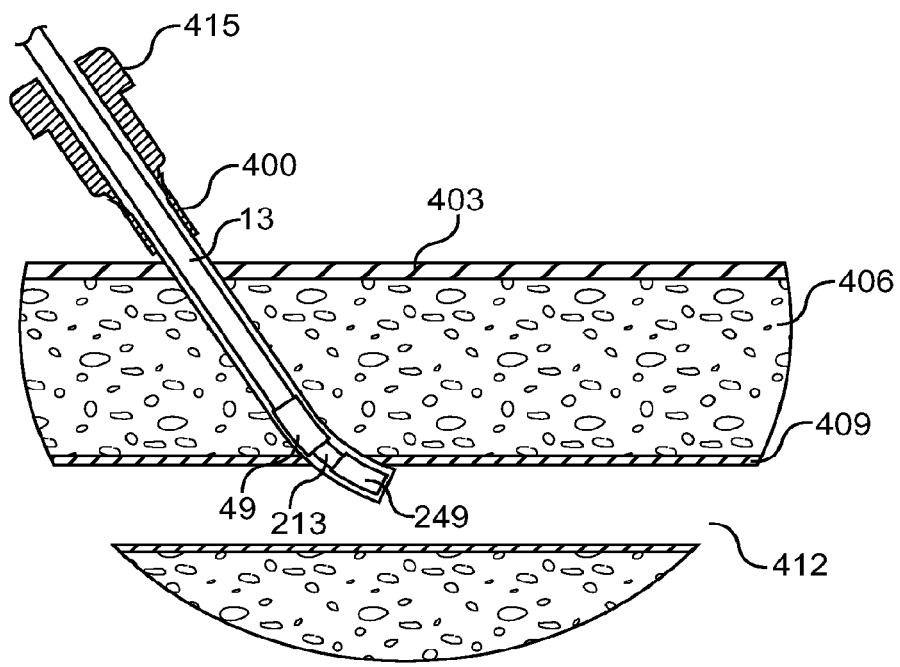
Figure 10C:
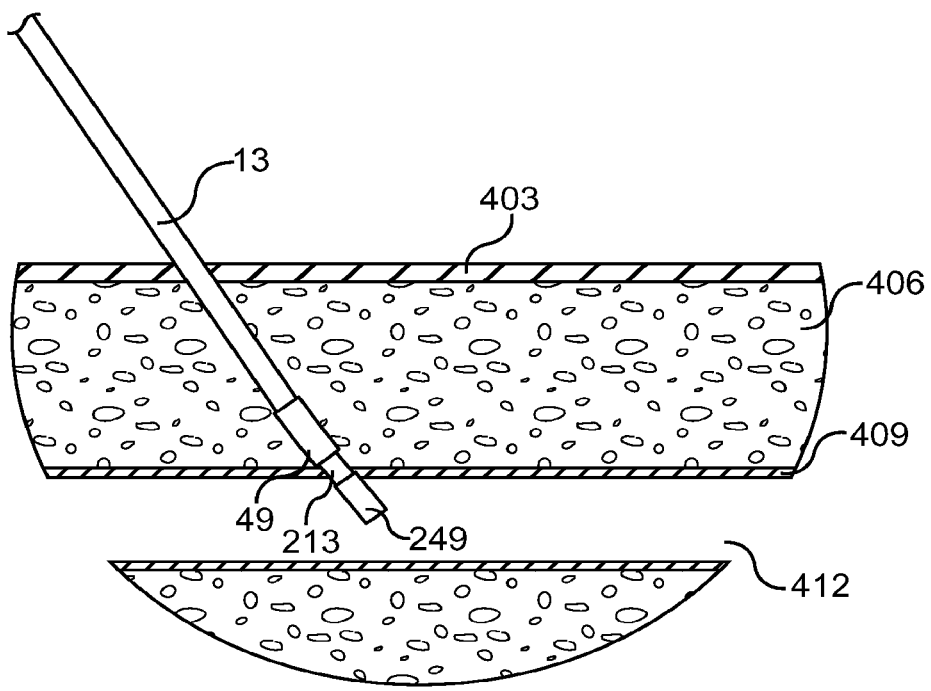

The another catheter 213 of the assembly 500 is preloaded within the lumen 43 of the internal tubular body 25 of the one catheter 13. The distal end of the assembly 500 is then inserted through a hub 415 of the sheath 400, thereby advancing the assembly 500 including both the one and another catheters through an opening in skin 403, through tissue tract 406. The another catheter 216 is advanced until the another expansible member is disposed within the body lumen 412 while the one catheter's expansible member 49 is placed at a predetermined distance from the vessel wall 409 within the tissue/fascia 406 (FIG. 10B). The introducer sheath 400 is then slowly pulled proximally and retracted (not shown) from the body lumen, with the one and another expansible members located in the tissue/fascia and the body lumen, respectively (FIG. 10C).

Figure 10D:
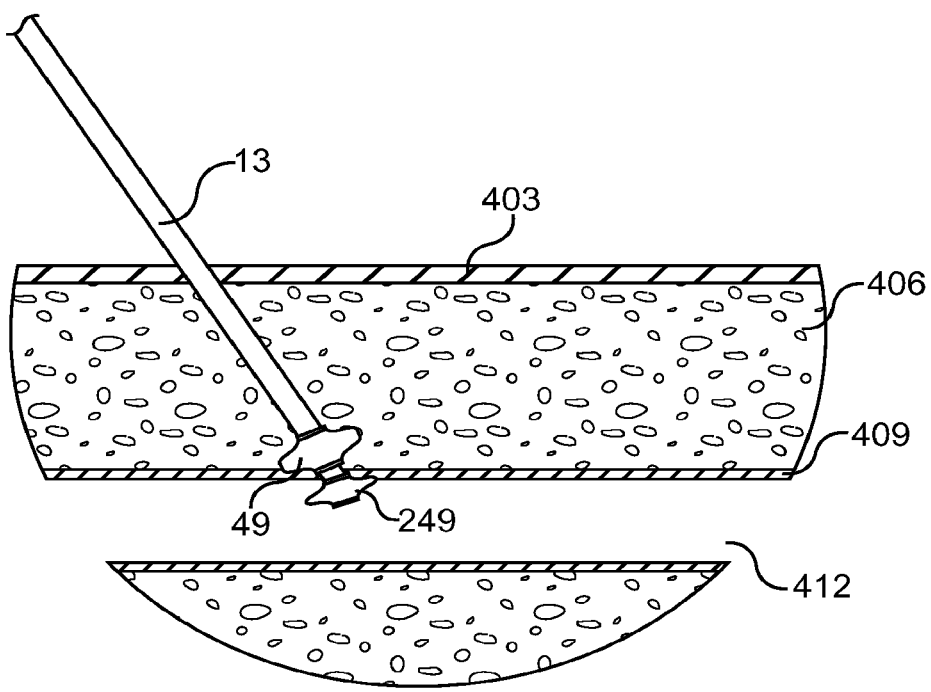
Figure 10E:
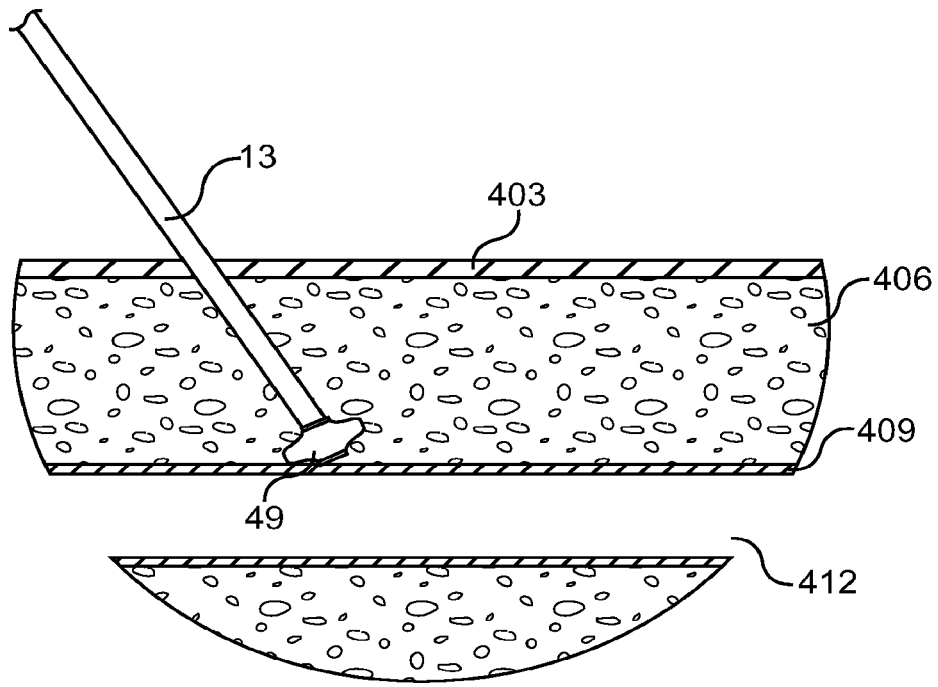

As shown in FIG. 10D, the one and the another expansible members are then expanded in their respective locations, with the one expansible member in the tissue/fascia and the another expansible member seating against the vessel wall at the puncture site within the body lumen.

Figure 10F:
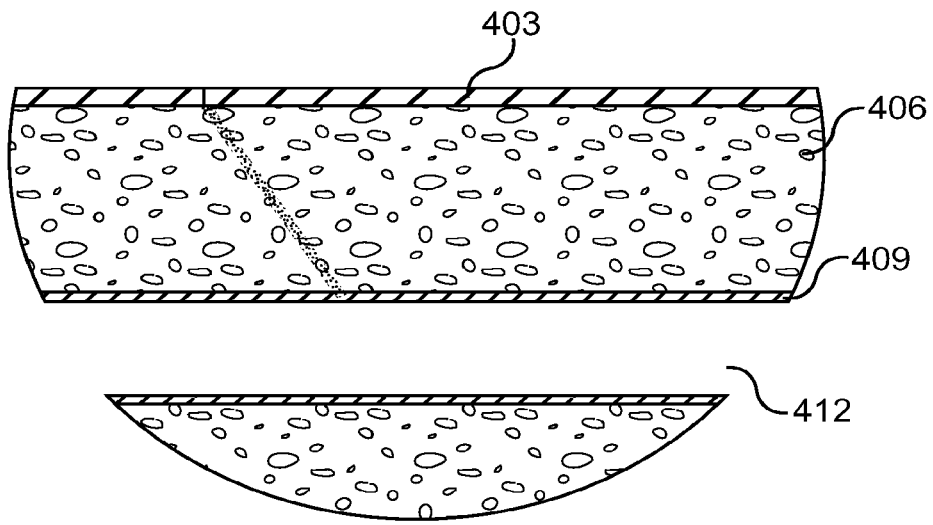

The another expansible member 249 is then contracted and the another catheter 213 is then pulled proximally and removed (not shown) from the body through the lumen of the one catheter 13, leaving one catheter and the one expansible member 49 in the tissue fascia (FIG. 10E) as long as necessary to allow the body's own natural wound healing mechanism to achieve hemostasis, after which it is removed from the patient's body (FIG. 10F). During the procedure, a syringe (not shown), may be used to draw bodily fluids, such as blood, from the body lumen through the lumen 43 of the internal tubular body 25. Alternatively, the one expansible member may be contracted and removed from the body lumen first, leaving the another expansible member in place as long as necessary before withdrawing it from the patient's body.

Figure 11A:
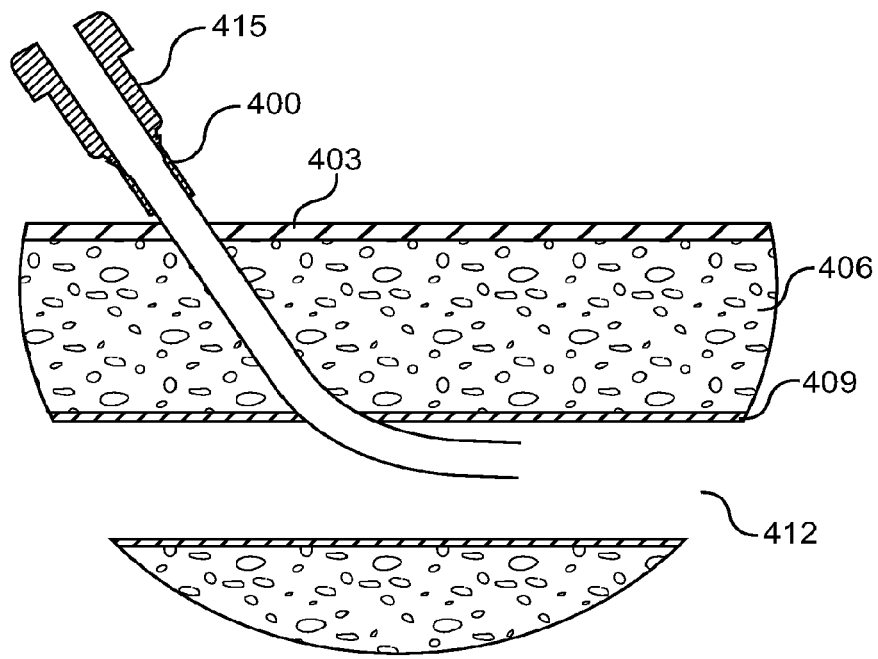
FIGS. 11A though 11E illustrate an exemplary method for hemostasis of a puncture site in a body lumen employing the devices shown in FIG. 6.
Figure 11B:
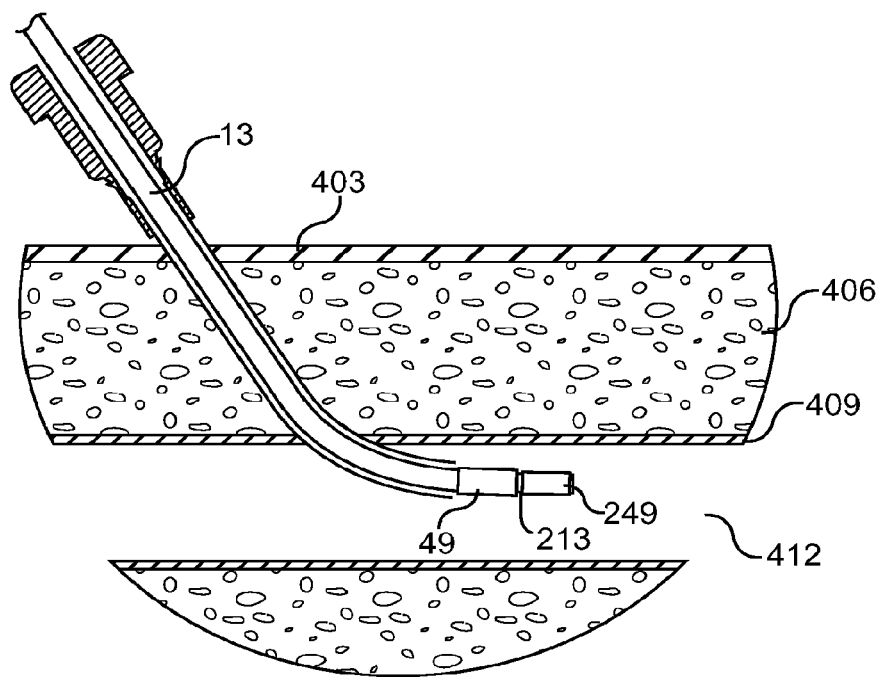

Referring now to FIGS. 11A through 11E, features of a method for hemostasis of a puncture site in a body lumen employing the assembly 500 comprising devices 10 and 11 of FIGS. 6-7 is illustrated. FIG. 11A depicts an existing introducer sheath 400 disposed through an opening in a skin surface 403, tissue tract in fascia 406, and vessel wall 409 and seated in a vessel lumen 412, at the completion of a catheterization procedure.

The another catheter 213 of the assembly 500 is preloaded within the lumen 43 of internal tubular body 25 of the one catheter 13. The distal end of the assembly 500 is then inserted through a hub of the sheath 400, thereby advancing the assembly 500 including both the one and another catheters through an opening in skin 403, through tissue tract 409.

With the one and the another expansible members positioned within the body lumen and expanded, the one expansible member rests against the vessel wall at the puncture site, while the another expansible member is placed against the distal end of the one expansible member.

Figure 11C:
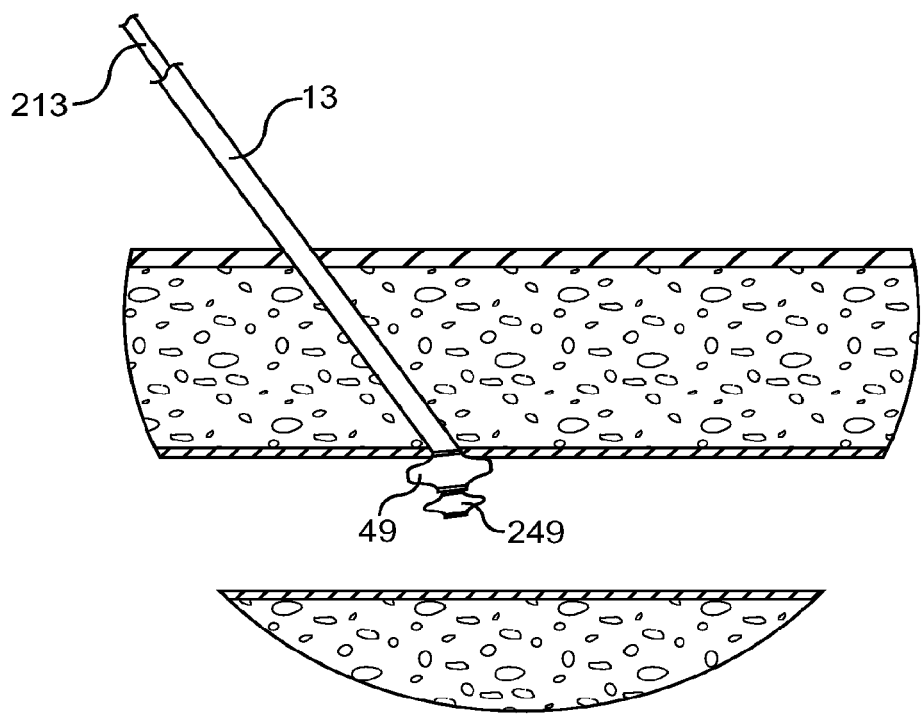
Figure 11D:
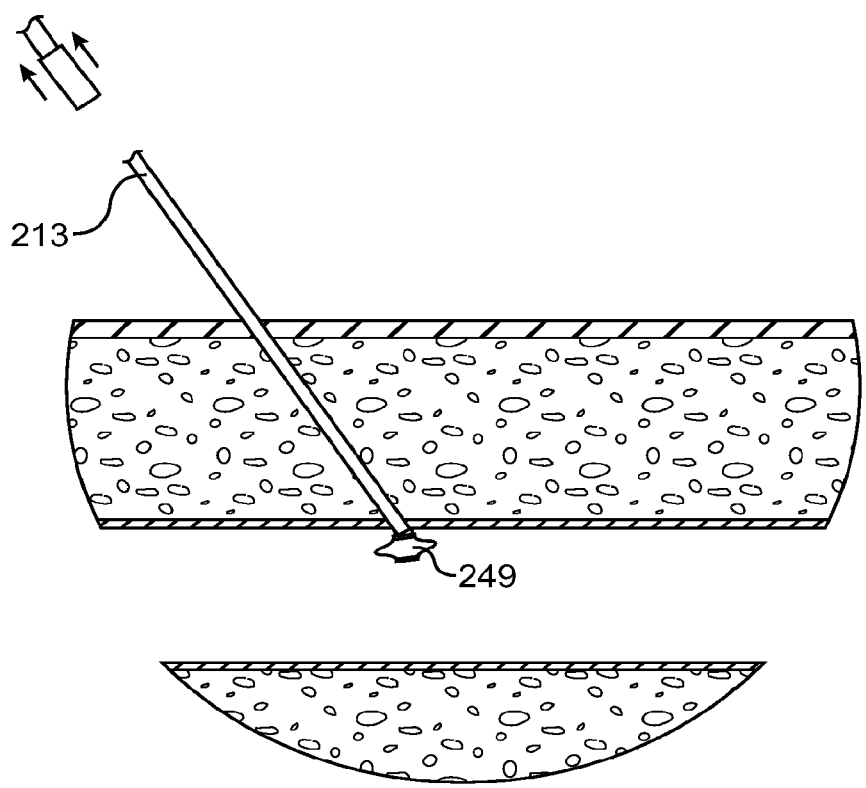

The introducer sheath 400 is then slowly pulled proximally and retracted (not shown) from the body lumen 412, leaving the first and second catheters in place within the body lumen (FIG. 11C).

Figure 11E:
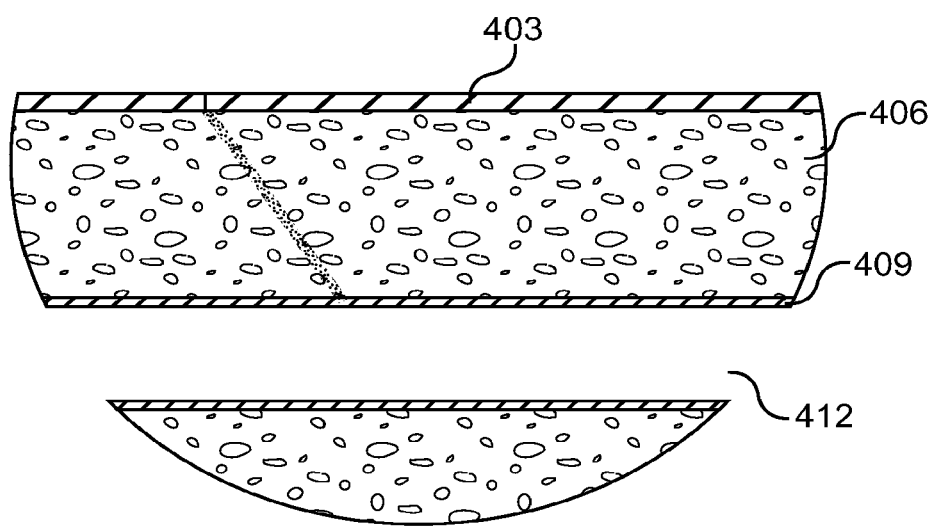

The one expansible member 49 is then contracted and the one catheter 13 is then pulled proximally and removed (FIG. 11D) from the body over the another catheter 213, leaving the another catheter and the another expansible member 249 in the body lumen as long as necessary to allow the body's own natural wound healing mechanism to achieve hemostasis, after which it is removed from the patient's body (FIG. 11E). During the procedure, a syringe (now shown), may be used to draw bodily fluids, such as blood, from the body lumen through the lumen 43 of the internal tubular body 25. Alternatively, the another expansible member may be contracted and removed from the body lumen first, leaving the one expansible member in place as long as necessary before withdrawing it from the patient's body.

Figure 12A:
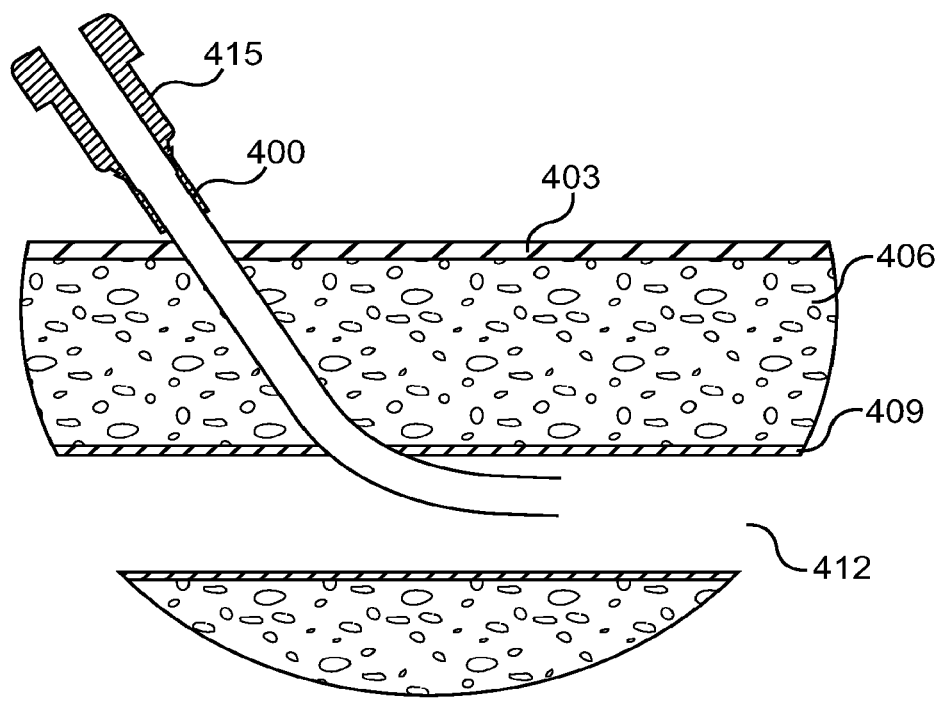
FIGS. 12A through 12H illustrate an exemplary method for hemostasis of a puncture site in a body lumen employing the devices shown in FIG. 6.

Now, referring to FIGS. 12A-12H and 13A-13G, features of an exemplary method for hemostasis of a puncture site in a body lumen employing the device 10 and 20 of FIGS. 6-7 is illustrated. FIGS. 12A and 13A depict an existing introducer sheath 400 disposed through an opening in a skin surface 403, tissue tract in fascia 406, and vessel wall 409 and seated in a vessel lumen 412, at the completion of a catheterization procedure.

Figure 12B:
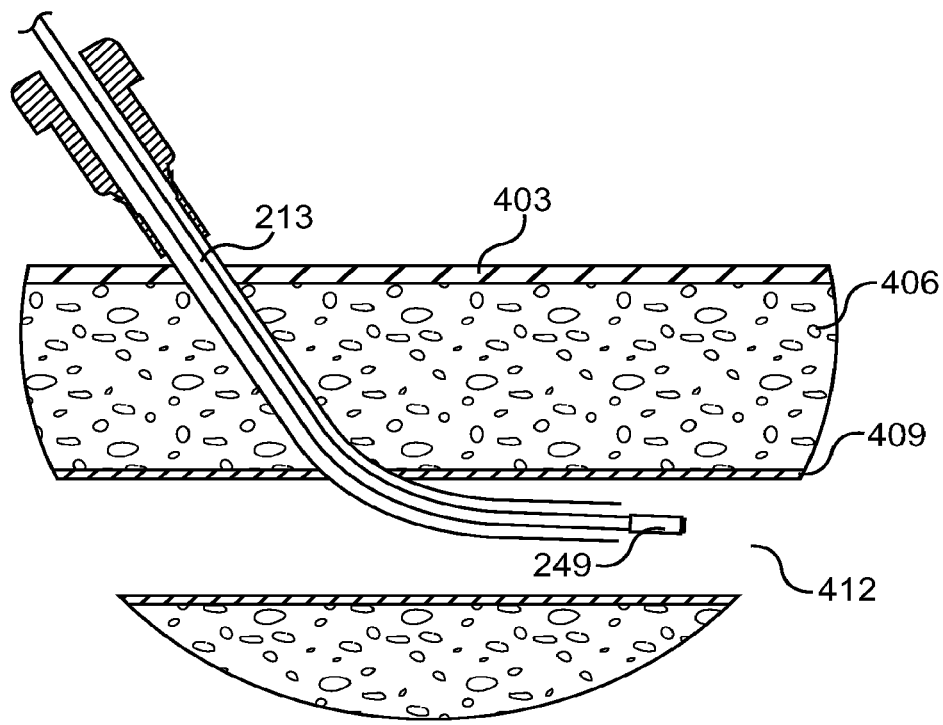
Figure 12C:
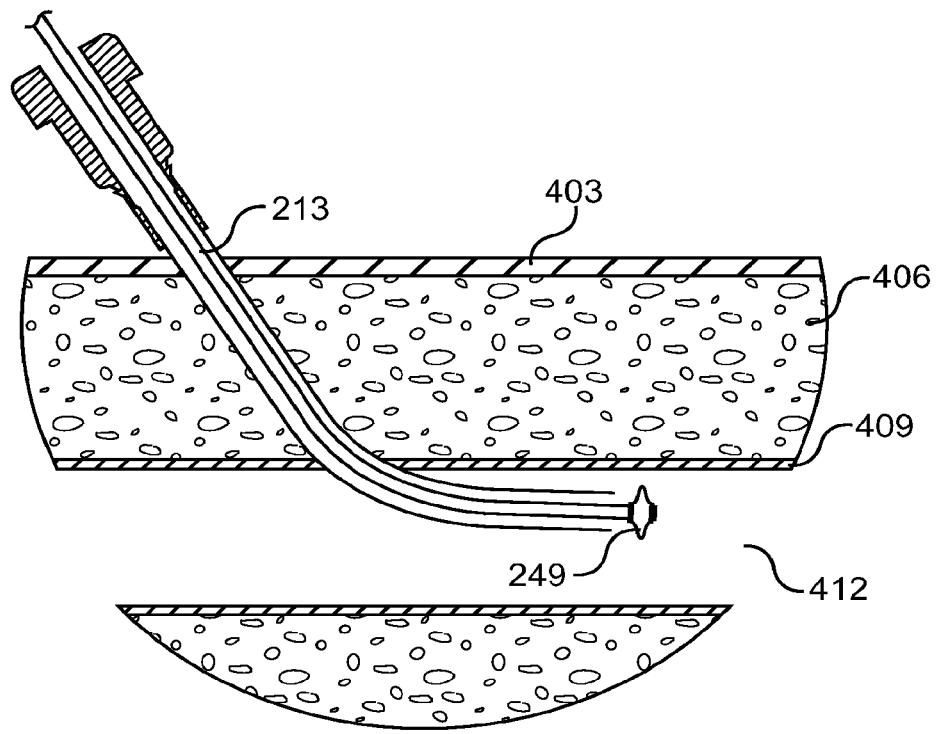
Figure 12D:
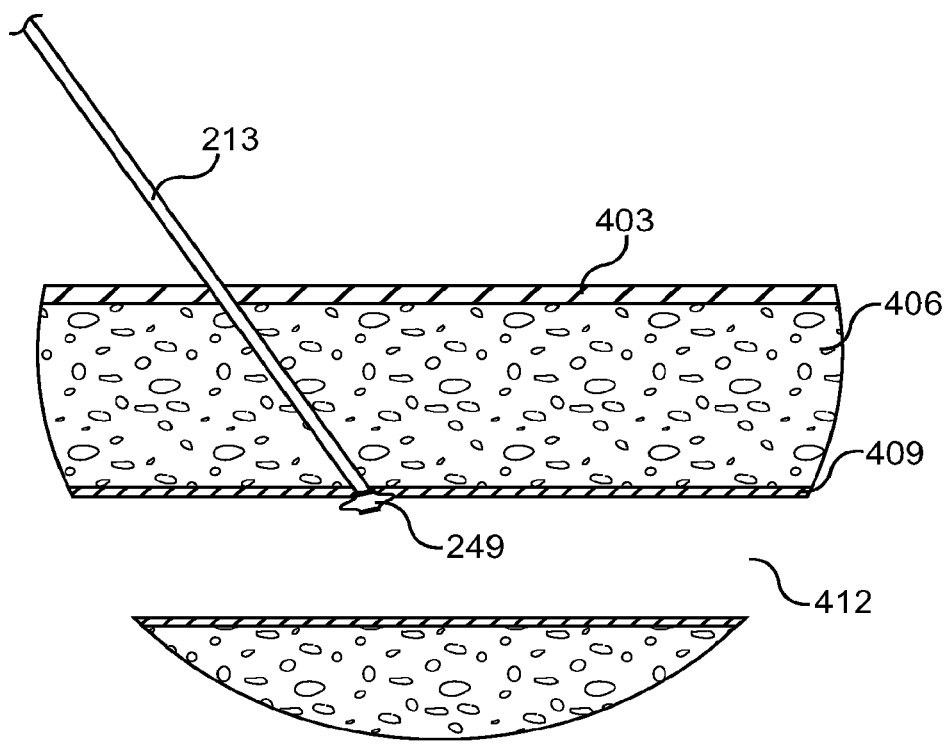
Figure 13A:
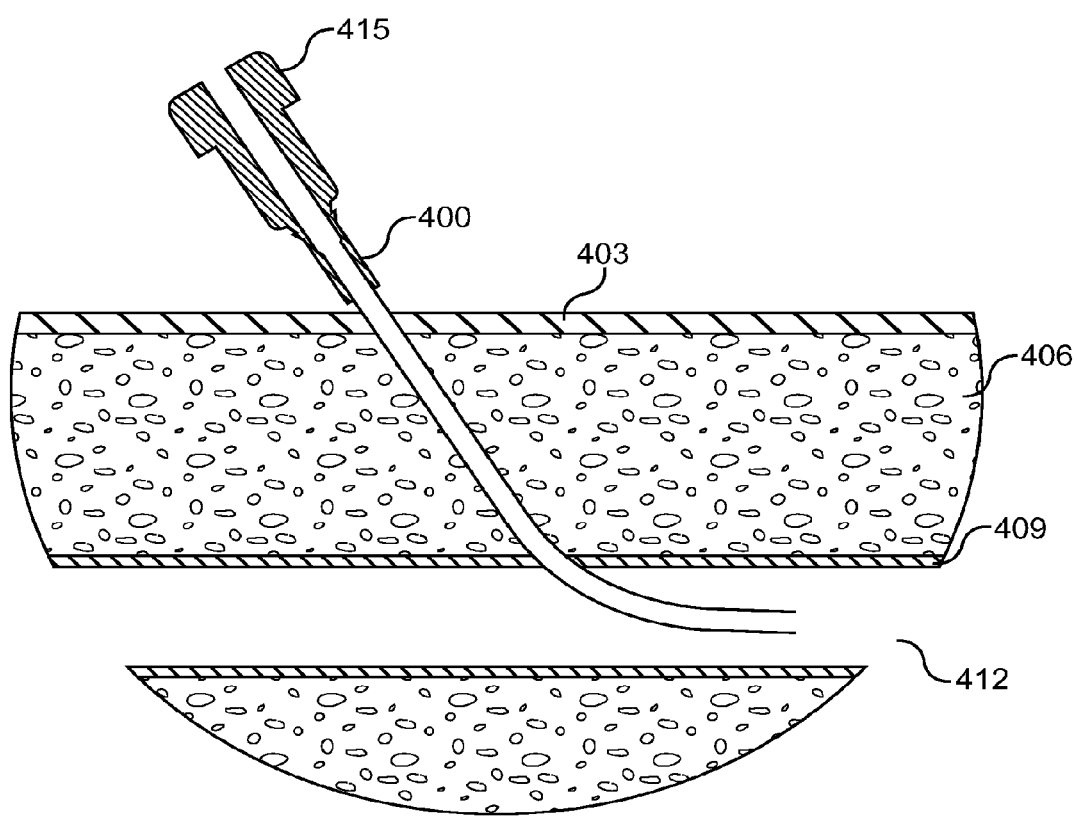
Figure 13B:
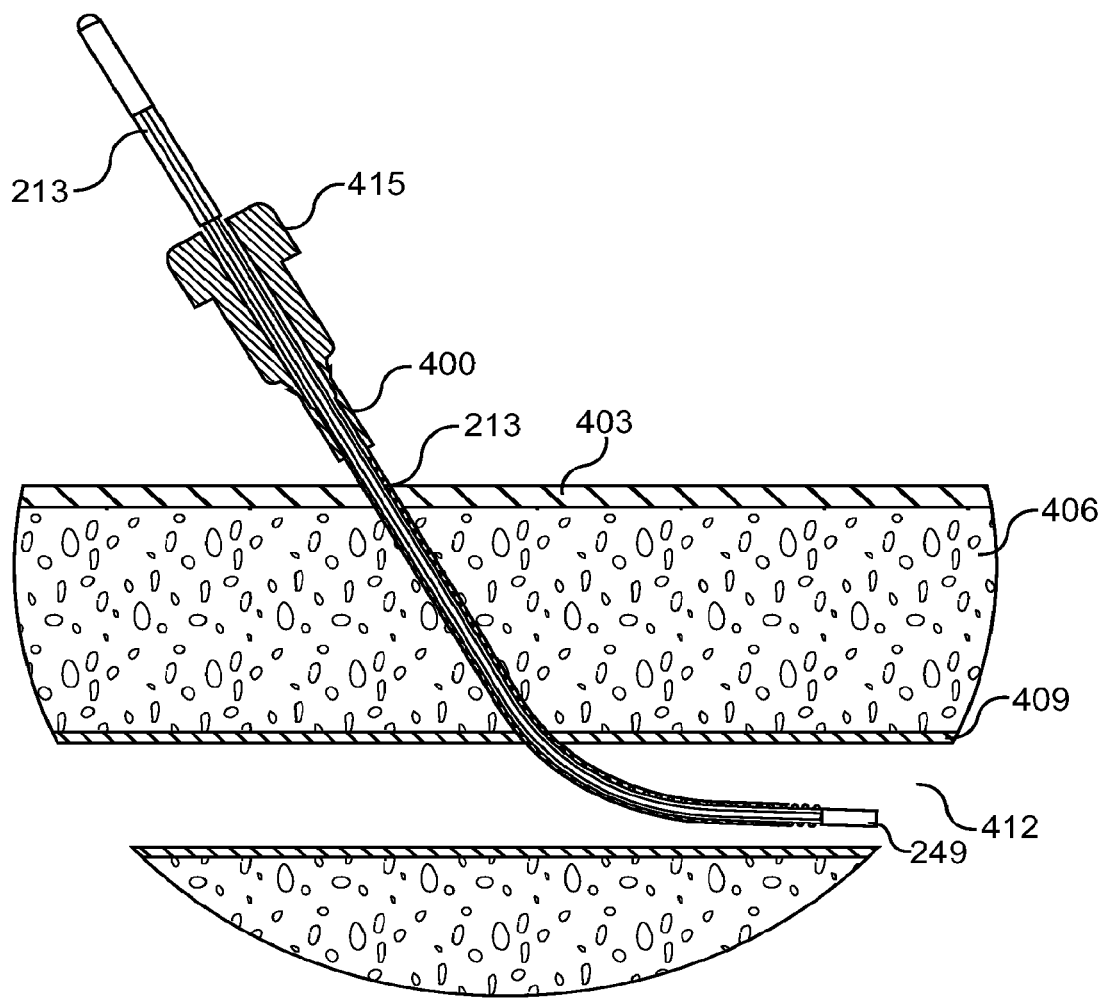
Figure 13C:
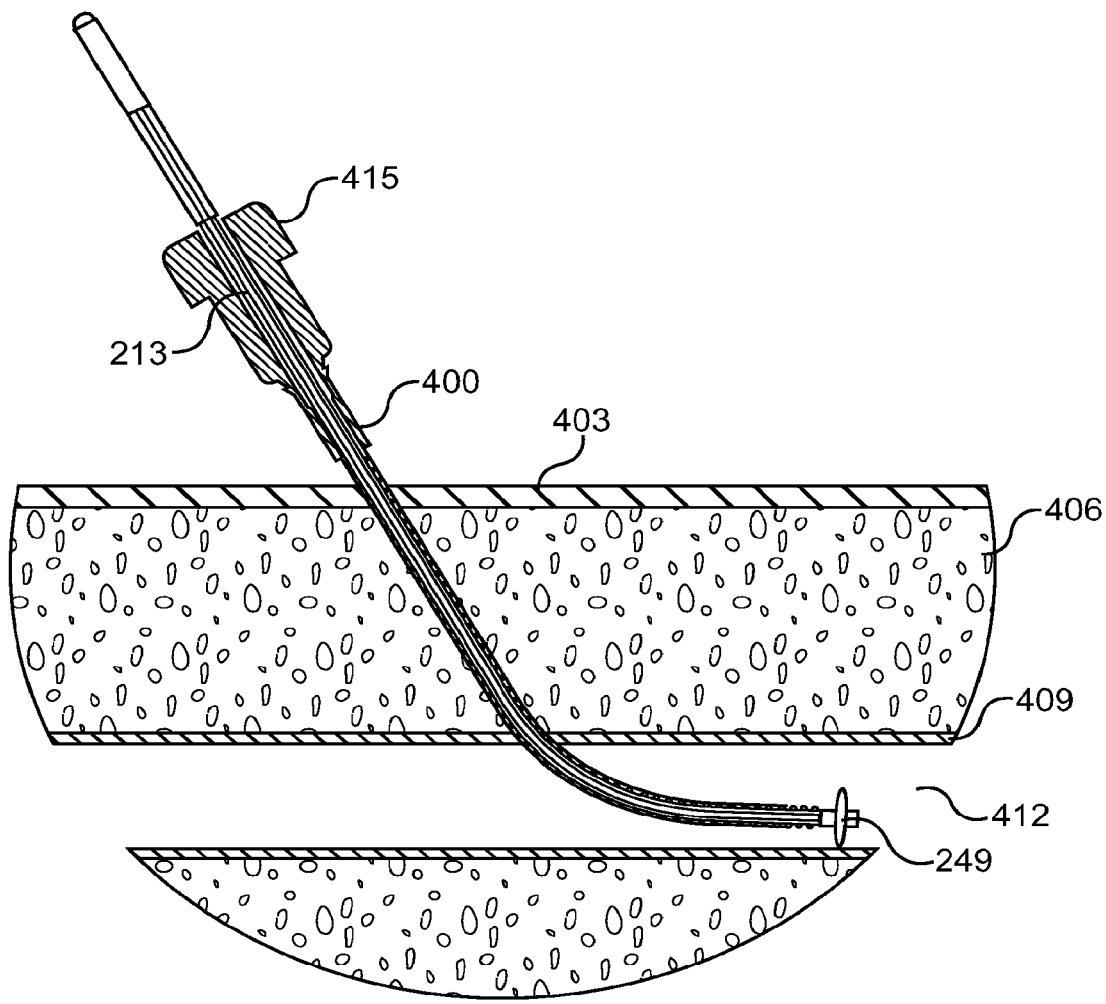
Figure 13D:
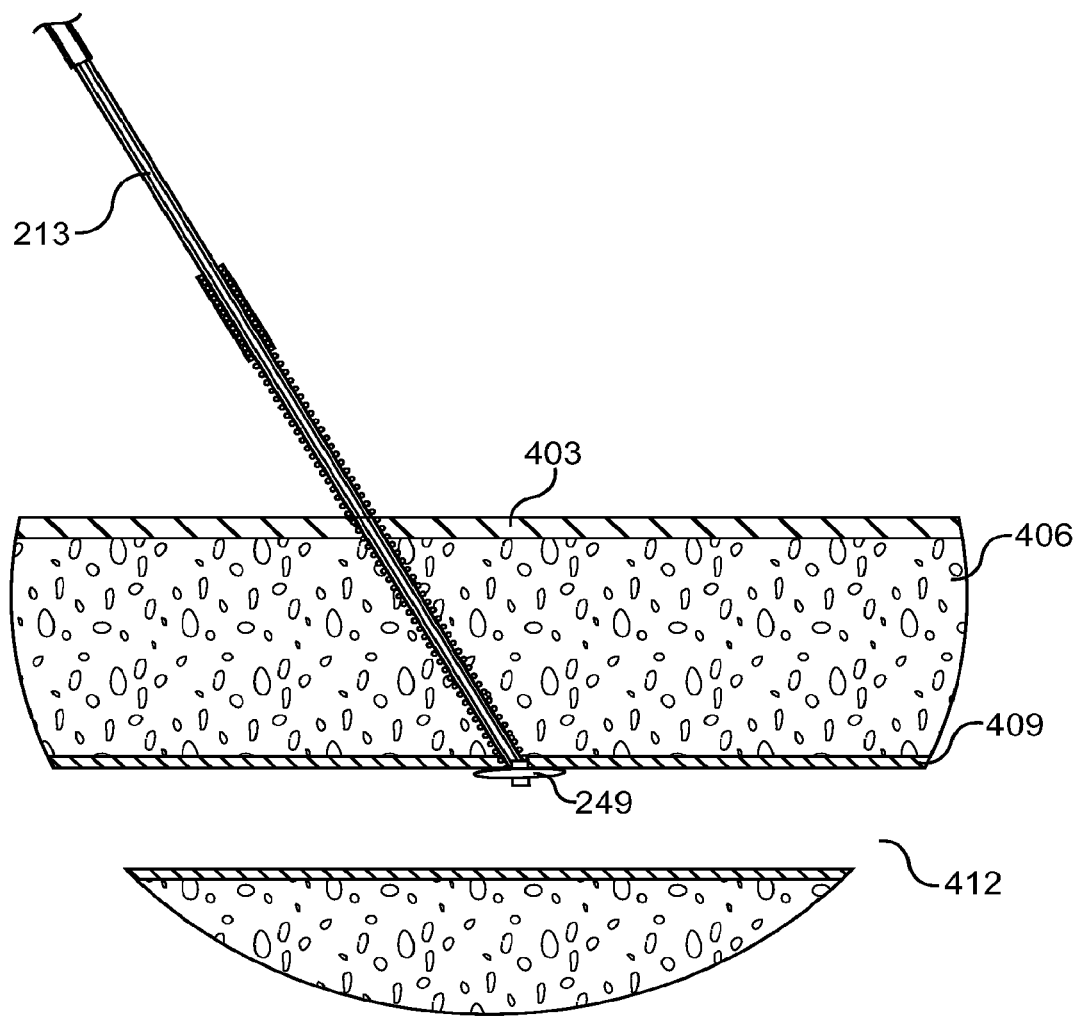

The another catheter 123 of the of device 20 is then inserted through a hub 415 of the sheath 400 to a marking, such as when the distal end of the distal handle part of the another catheter rests against the hub of the sheath, as shown in FIGS. 12B and 13B, thereby advancing the another expansible member 249 within the body lumen 412. As shown in FIGS. 12C and 13C, the another expansible member 249 is then expanded by holding the distal handle part 286 of another catheter handle assembly stationary and moving the proximal handle part 283 proximally. The introducer sheath 400 is then slowly pulled proximally and retracted from the body lumen (not shown), leaving the another catheter in place with the another expansible member in expanded position seating against the vessel wall at the puncture site within the body lumen (FIGS. 12D and 13D).

Figure 12E:
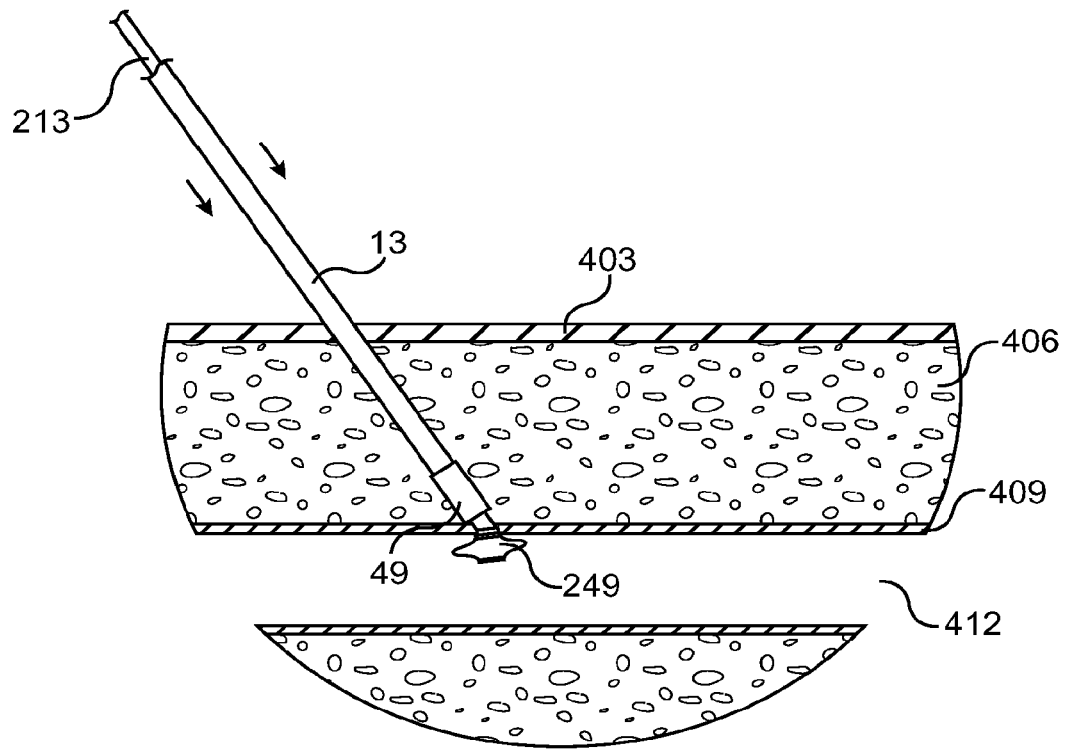
Figure 12F:
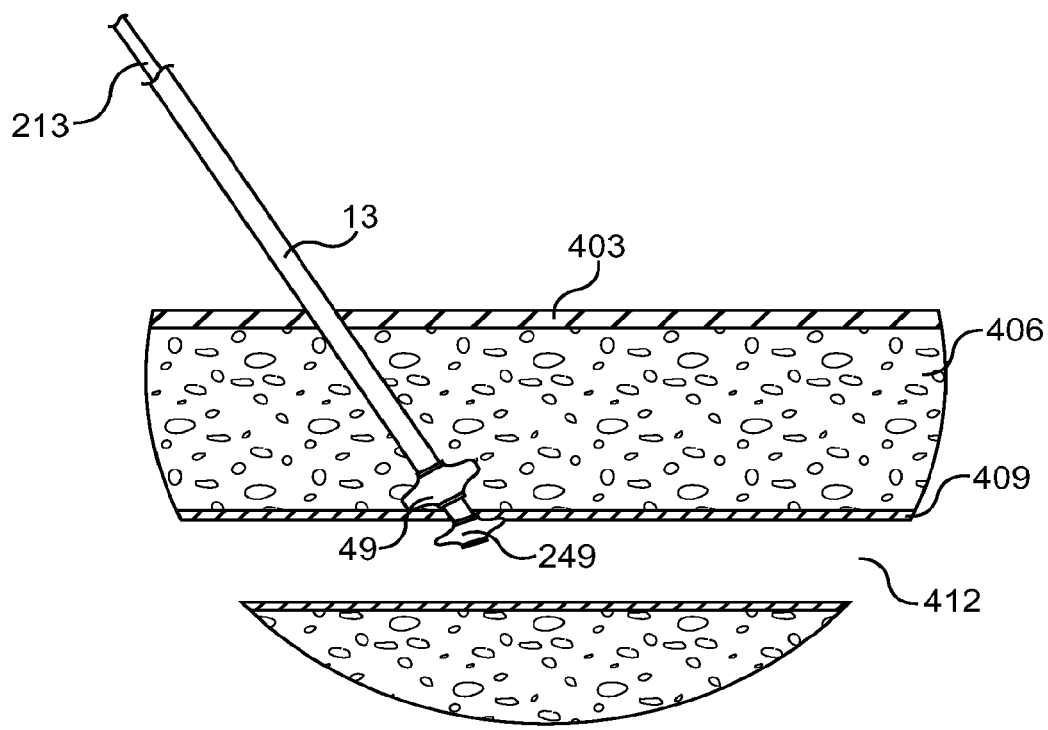
Figure 12G:
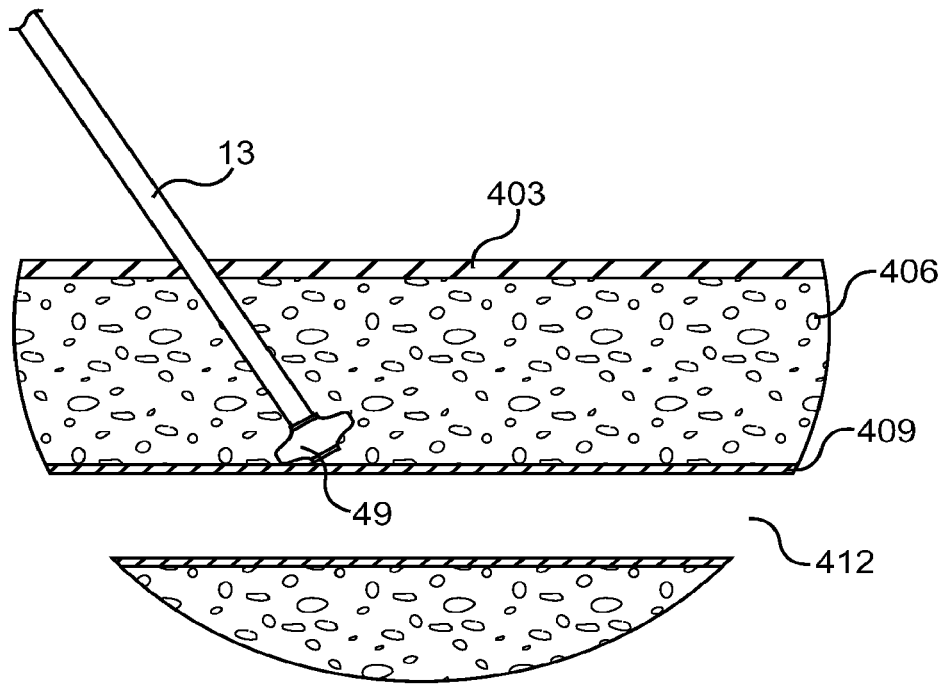
Figure 13F:
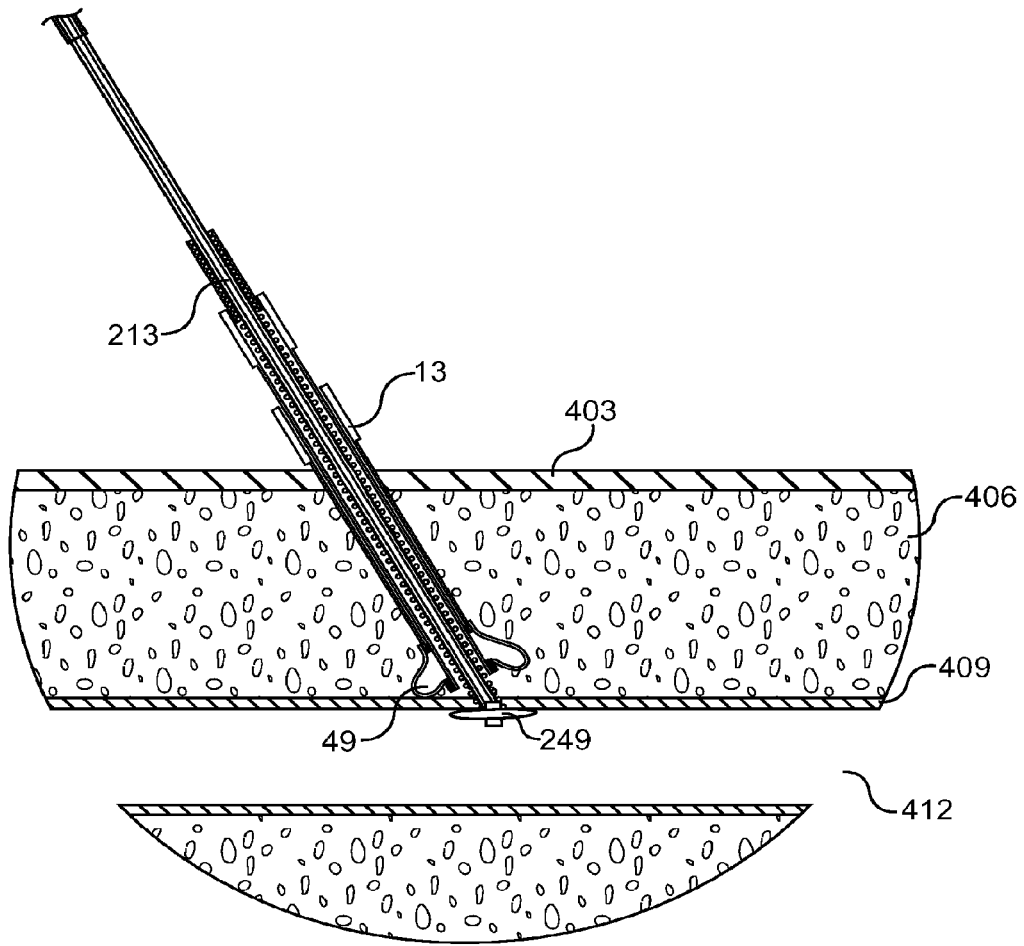
Figure 13G:
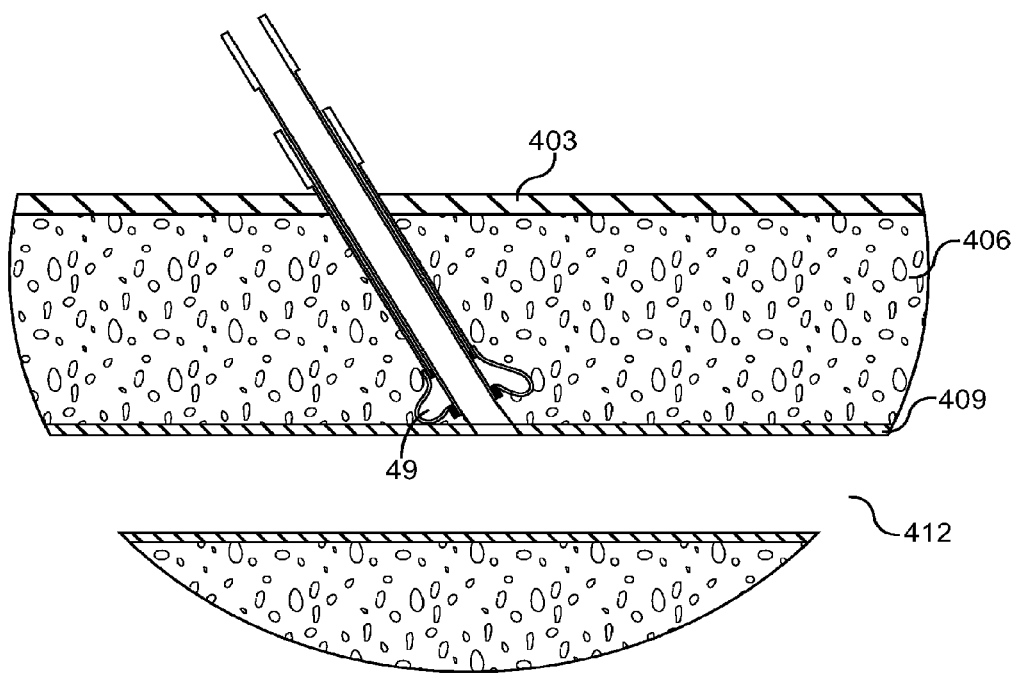

Now referring to FIGS. 12E and 13E1-E2, the proximal end of the another catheter 213 is pushed through the distal end of the one catheter 13 and fed through the lumen of its internal tubular body until it exits the proximal end of the one catheter. The one catheter is then guided over the tubular member of the another catheter through an opening in skin, through tissue tract, until its distal end is placed at a predetermined distance from the vessel wall and against subcutaneous tissue. The one expansible member is then expanded over the puncture site of the vessel wall by pulling the handle of the external tubular body proximally while maintaining the internal tubular body of the one catheter substantially stationary (FIGS. 12F and 13F).

Figure 12H:
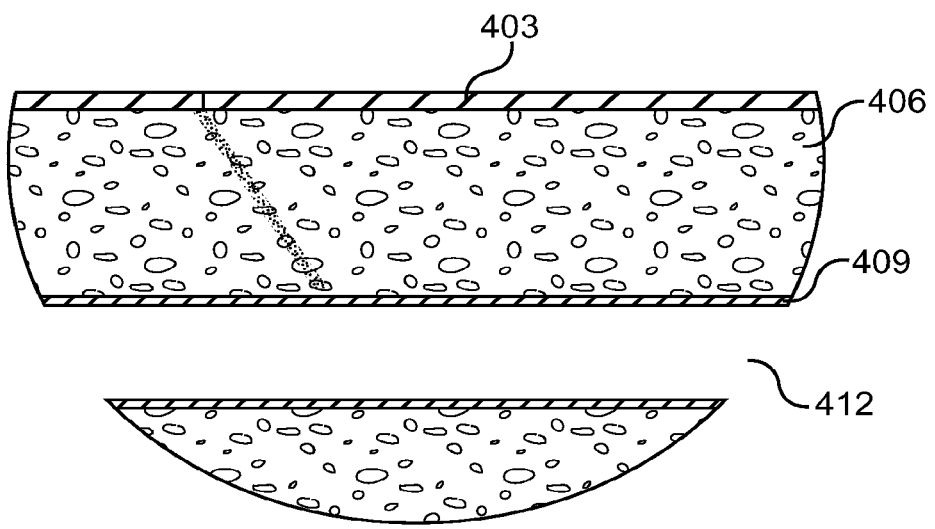

The another expansible member 249 is then contracted and the another catheter 123 is then pulled proximally and removed (not shown) from the body through the lumen of the one catheter, leaving the one catheter and the one expansible member in the tissue fascia (FIGS. 12G and 13G) as long as necessary to allow the body's own natural wound healing mechanism to achieve hemostasis, after which it is removed from the patient's body (FIG. 12H). During the procedure, the syringe, as for example shown in FIG. 1C, may be used to draw bodily fluids, such as blood, from the body through the lumen of the internal tubular body.

As can be appreciated, the catheters of assembly 500 may be advanced, expanded, and retracted from the patient's body in any order as may be necessary. Additionally, each of the one expansible member and the another expansible members, when used in combination with one another, may, independently, be expanded within the body lumen or within the tissue/fascia.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A device for enhancing the hemostasis of a puncture site in a body lumen or tract, the device comprising:
    an outer tubular body having a proximal end and, a distal end, and a lumen extending there between;
    an inner tubular body longitudinally movable within the lumen of the outer tubular body, said inner tubular body having a proximal end, a distal end, and an inner lumen extending there between;
    an expansible member connected between the distal ends of internal tubular body and the external tubular body, wherein said expansible member can be shifted between an expanded configuration for sealing against a blood vessel wall penetration and an unexpanded configuration; and
    a seal or syringe/hemostatic valve connector having a distal end and a proximal end, the distal end of the seal or syringe/hemostatic valve connector being fixedly attached to the proximal end of the inner tubular member, said seal or syringe/hemostatic valve connector being configured to provide for fluid delivery or blood removal through the inner lumen of the inner tubular body, the inner lumen of the inner tubular body terminating in the proximal direction with the distal end of the seal or syringe/hemostatic valve connector at the proximal end of the inner tubular body.

2. A device as in claim 1, wherein the degree of expansion of the expansible member is based on a longitudinal displacement between the external and the internal tubular bodies.

3. A device as in claim 2, wherein the expansible member comprises a braided filament, mesh layer, spring, coil, slotted tube, or coiled string.

4. A device as in claim 3, wherein the expansible member comprises a braided filament having small pores.

5. A device as in claim 4, wherein in the unexpanded configuration the internal diameter of the expansible member at a distal end thereof is smaller than an internal diameter of the expansible member at a proximal end thereof.

6. A device as in claim 1, wherein the expansible member is configured to fold forward in the expanded configuration.

7. A device as in claim 1, wherein the expansible member is configured for expansion intraluminally within the body lumen at the puncture site.

8. A device as in claim 1, wherein the expansible member is configured for expansion extraluminally within a fascia along a tissue tract of the puncture site.

9. A device as in claim 1, wherein the expansible member is at least partially covered with a membrane.

10. A device as in claim 1, wherein the seal or syringe/hemostatic valve is configured to couple to a fluid delivery or blood removal apparatus to provide for fluid delivery or blood removal through the inner lumen of the inner tubular body.

11. A device as in claim 10, wherein the inner tubular body defines a longitudinal axis, and wherein the seal or syringe/hemostatic valve is configured to be coupled to the fluid delivery or blood removal apparatus such that the fluid delivery or blood removal apparatus is coaxial with the longitudinal axis of the inner tubular body.

12. A device as in claim 10, wherein the fluid delivery or blood removal apparatus comprises a syringe.

* * * * *